United States Patent
Takahashi et al.

(10) Patent No.: US 9,345,395 B2
(45) Date of Patent: May 24, 2016

(54) IMAGING MODULE AND ENDOSCOPE DEVICE

(71) Applicant: OLYMPUS CORPORATION, Tokyo (JP)

(72) Inventors: Tomohisa Takahashi, Hachioji (JP); Hironobu Ichimura, Akishima (JP); Tatsuya Daimaru, Hachioji (JP); Tomokazu Yamashita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/666,784

(22) Filed: Mar. 24, 2015

(65) Prior Publication Data
US 2015/0190039 A1    Jul. 9, 2015

Related U.S. Application Data

(63) Continuation of application No. PCT/JP2014/059817, filed on Apr. 3, 2014.

(30) Foreign Application Priority Data

Jun. 28, 2013 (JP) .................................. 2013-136755

(51) Int. Cl.
*A61B 1/05* (2006.01)
*A61B 1/00* (2006.01)
(Continued)

(52) U.S. Cl.
CPC ............... *A61B 1/05* (2013.01); *A61B 1/00009* (2013.01); *A61B 1/0011* (2013.01);
(Continued)

(58) Field of Classification Search
CPC ...... A61B 1/05; A61B 1/051; G02B 23/2484; H04N 5/2257; H04N 2005/2255
USPC .................................................... 348/76, 340
See application file for complete search history.

(56) References Cited

U.S. PATENT DOCUMENTS 4,677,471 A * 6/1987 Takamura ................ A61B 1/05
                                                  348/373
4,706,654 A * 11/1987 Ogiu ........................ A61B 1/05
                                                  348/E5.026

(Continued)

FOREIGN PATENT DOCUMENTS

JP         09-098944 A      4/1997
JP         2000-201884 A    7/2000

(Continued)

OTHER PUBLICATIONS

International Search Report dated May 13, 2014 issued in PCT/JP2014/059817.

*Primary Examiner* — John P Leubecker
(74) *Attorney, Agent, or Firm* — Scully, Scott, Murphy & Presser, P.C.

(57) ABSTRACT

An imaging module includes: a solid-state imaging element including a light receiving face for receiving light; a mounting substrate including a connection portion which is located inside an imaging element projection area that is a projection area where the solid-state imaging element is projected in an optical axis direction and which is connected to a back surface of the solid-state imaging element on a distal end side of the mounting substrate, the mounting substrate on a rear end side being extended in the optical axis direction; and a metallic reinforcing member that has a sleeve shape open at both ends and covers the solid-state imaging element and the connection portion of the mounting substrate along the optical axis direction in a state where an inner circumferential surface of the reinforcing member is away from the solid-state imaging element and the mounting substrate.

5 Claims, 16 Drawing Sheets

(51) Int. Cl.
  *G02B 23/24* (2006.01)
  *A61B 1/06* (2006.01)
  *H04N 5/225* (2006.01)
  *H04N 5/369* (2011.01)

(52) U.S. Cl.
  CPC ........ *A61B 1/00018* (2013.01); *A61B 1/00096* (2013.01); *A61B 1/051* (2013.01); *A61B 1/0669* (2013.01); *G02B 23/2423* (2013.01); *G02B 23/2484* (2013.01); *H04N 5/2257* (2013.01); *H04N 5/369* (2013.01); *H04N 2005/2255* (2013.01)

(56) References Cited

U.S. PATENT DOCUMENTS

| | | | | |
|---|---|---|---|---|
| 4,918,521 | A * | 4/1990 | Yabe | A61B 1/00179 348/373 |
| 5,021,888 | A * | 6/1991 | Kondou | A61B 1/05 348/76 |
| 5,220,198 | A * | 6/1993 | Tsuji | A61B 1/05 257/680 |
| 5,857,963 | A * | 1/1999 | Pelchy | A61B 1/05 348/373 |
| 6,142,930 | A * | 11/2000 | Ito | A61B 1/00096 348/76 |
| 6,567,115 | B1 * | 5/2003 | Miyashita | A61B 1/051 348/76 |
| 6,635,865 | B1 * | 10/2003 | Soltyk | H04N 1/02805 250/208.1 |
| 2006/0004256 | A1 * | 1/2006 | Gilad | A61B 1/041 600/160 |
| 2008/0100732 | A1 * | 5/2008 | Minamio | H04N 5/2251 348/294 |
| 2009/0253955 | A1 | 10/2009 | Akiba | |
| 2009/0268019 | A1 * | 10/2009 | Ishii | A61B 1/00124 348/65 |
| 2011/0245600 | A1 * | 10/2011 | Ishii | A61B 1/05 600/104 |

FOREIGN PATENT DOCUMENTS

| | | |
|---|---|---|
| JP | 2003-209751 A | 7/2003 |
| JP | 2007-068563 A | 3/2007 |
| WO | WO 2011/092903 A1 | 8/2011 |

\* cited by examiner

IMAGING MODULE AND ENDOSCOPE DEVICE

CROSS-REFERENCE TO RELATED APPLICATIONS

This application is a continuation of PCT international application Ser. No. PCT/JP2014/059817 filed on Apr. 3, 2014 which designates the United States, incorporated herein by reference, and which claims the benefit of priority from Japanese Patent Application No. 2013-136755, filed on Jun. 28, 2013, incorporated herein by reference.

BACKGROUND

1. Technical Field

The disclosure relates to an imaging module and an endoscope device including an insertion portion provided with the imaging module at a distal end thereof.

2. Related Art

Conventionally, in the medical field and the industrial field, endoscope devices are widely used for various examinations. Among them, a medical endoscope device can acquire an in-vivo image in a body cavity without incising a subject by inserting a flexible insertion portion, which has an elongated shape and which is provided with an imaging element at its distal end, into the body cavity of the subject such as a patient, and further the medical endoscope device can perform remedial treatment by projecting a treatment tool from the distal end of the insertion portion if necessary. Therefore, the medical endoscope device is widely used.

In such an endoscope device, an imaging module including the imaging element and a lens unit that forms an object image on a light receiving face provided on a surface of the imaging element are fitted into a rigid holding frame inside the distal end of the insertion portion. Then, as the imaging module, a mounting substrate on which an electronic component for driving the imaging element is mounted is arranged to be located within a projection area of the imaging element. In the case of the endoscope device, when the insertion portion is bent, there is a risk that a stress is applied to a connection portion between the imaging element and the mounting substrate through a signal cable extended in the insertion portion. To prevent the connection portion between the imaging element and the mounting substrate from being broken when such an external force is applied, at least a metallic reinforcing member for protecting the connection portion between the imaging element and the mounting substrate from the external force is fitted into the holding frame in the distal end of the insertion portion (for example, see Japanese Patent Application Laid-open No. 2007-68563). Here, to avoid influence from outside, such as static electricity and disturbance noise, to the imaging element, the mounting substrate, and the electronic component, the reinforcing member is placed sufficiently away from the imaging element, the mounting substrate, and the electronic component, and insulated from the imaging element, the mounting substrate, and the electronic component.

SUMMARY

In some embodiments, an imaging module includes: a solid-state imaging element including a light receiving face for receiving light on a surface of the solid-state imaging element; a glass lid attached to the solid-state imaging element so as to cover the light receiving face of the solid-state imaging element; a mounting substrate including a connection portion which is located inside an imaging element projection area that is a projection area where the solid-state imaging element is projected in an optical axis direction of the solid-state imaging element and which is connected and fixed to a back surface of the solid-state imaging element on a distal end side of the mounting substrate, the mounting substrate on a rear end side being extended in the optical axis direction; a plurality of electronic components mounted on the mounting substrate; a metallic reinforcing member that has a sleeve shape open at both ends and covers the solid-state imaging element and the connection portion of the mounting substrate along the optical axis direction in a state where an inner circumferential surface of the reinforcing member is away from the solid-state imaging element and the mounting substrate; and a solid-state imaging element holder in which an outer circumferential surface of the glass lid is fitted into an inner circumferential surface of a proximal end side of the solid-state imaging element holder to hold the solid-state imaging element, the inner circumferential surface of a distal end side of the reinforcing member being fitted into an outer circumferential surface of the proximal end side of the solid-state imaging element holder. On a rear end side of the connection portion, the mounting substrate includes a protrusion portion that protrudes outside of the imaging element projection area in a state where the protrusion portion is away from a rear end of the reinforcing member by a specified distance or more. On the rear end side of the connection portion, the plurality of electronic components are mounted on the mounting substrate such that a longitudinal direction of the plurality of electronic components is perpendicular to the optical axis direction, and the plurality of electronic components are arranged away from the rear end of the reinforcing member by the specified distance or more.

In some embodiments, an endoscope device includes an insertion portion provided with an imaging module at a distal end of the insertion portion. The imaging module includes: a solid-state imaging element including a light receiving face for receiving light on a surface of the solid-state imaging element; a glass lid attached to the solid-state imaging element so as to cover the light receiving face of the solid-state imaging element; a mounting substrate including a connection portion which is located inside an imaging element projection area that is a projection area where the solid-state imaging element is projected in an optical axis direction of the solid-state imaging element and which is connected and fixed to a back surface of the solid-state imaging element on a distal end side of the mounting substrate, the mounting substrate on a rear end side being extended in the optical axis direction; a plurality of electronic components mounted on the mounting substrate; a metallic reinforcing member that has a sleeve shape open at both ends and covers the solid-state imaging element and the connection portion of the mounting substrate along the optical axis direction in a state where an inner circumferential surface of the reinforcing member is away from the solid-state imaging element and the mounting substrate; and a solid-state imaging element holder in which an outer circumferential surface of the glass lid is fitted into an inner circumferential surface of a proximal end side of the solid-state imaging element holder to hold the solid-state imaging element, the inner circumferential surface of a distal end side of the reinforcing member being fitted into an outer circumferential surface of the proximal end side of the solid-state imaging element holder. On a rear end side of the connection portion, the mounting substrate includes a protrusion portion that protrudes outside of the imaging element projection area in a state where the protrusion portion is away from a rear end of the reinforcing member by a specified distance or more. On the rear end side of the connection portion, the plurality of electronic components are mounted on the mounting substrate such that a longitudinal direction of the plurality of electronic components is perpendicular to the optical axis direction, and the plurality of electronic components are arranged away from the rear end of the reinforcing member by the specified distance or more.

The above and other features, advantages and technical and industrial significance of this invention will be better understood by reading the following detailed description of presently preferred embodiments of the invention, when considered in connection with the accompanying drawings.

DETAILED DESCRIPTION

An endoscope device including an imaging unit will be described below as modes for carrying out the invention (hereinafter referred to as "embodiments"). The present invention is not limited by the embodiments. The same reference signs are used to designate the same elements throughout the drawings. The drawings are schematic, and it is be noted that the relation between the thickness and the width of each member and the ratio of the size of each member are different from the reality. The size and the ratio of the same component may be different in different figures.

FIRST EMBODIMENT

Figure 1:
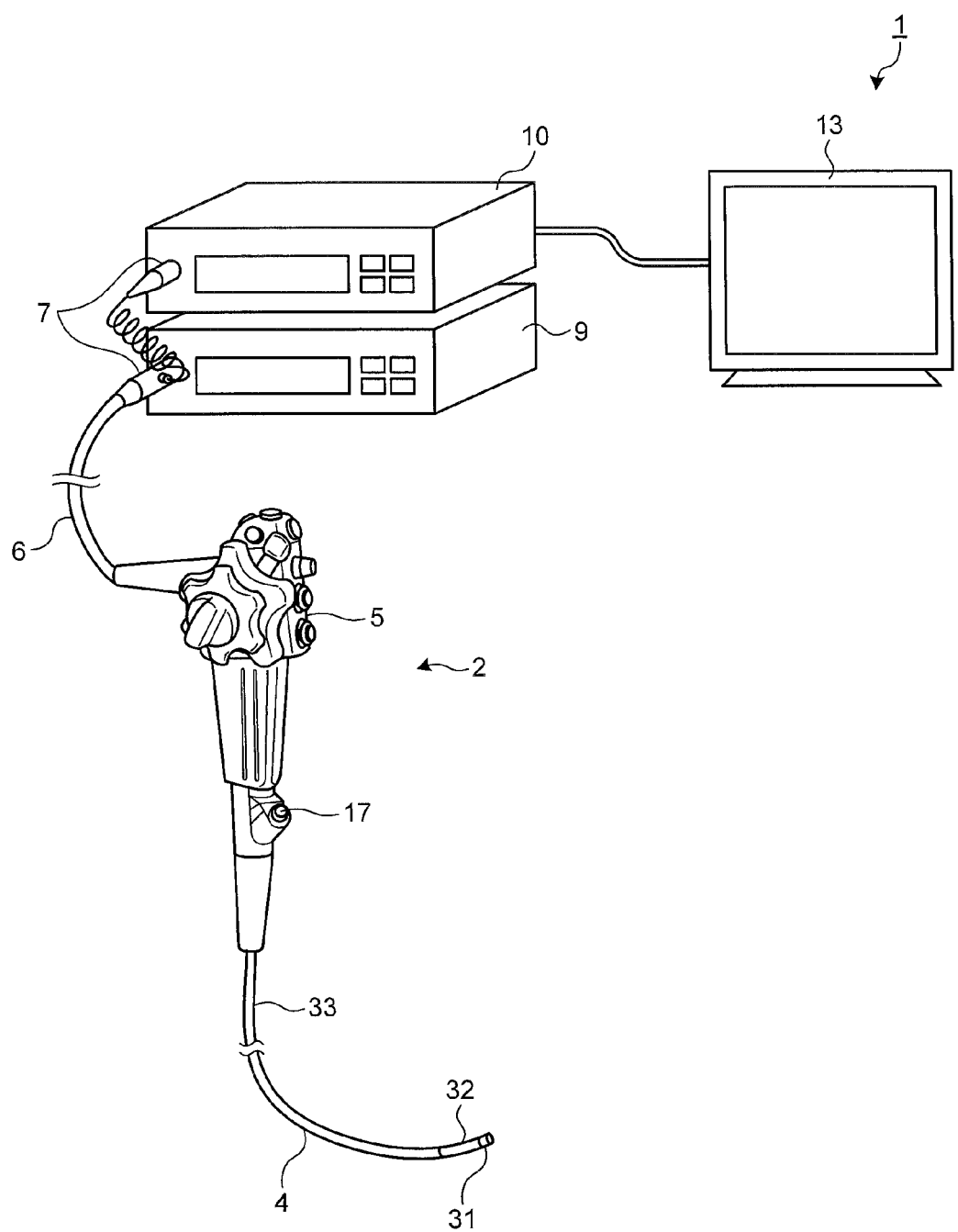
FIG. 1 is a diagram schematically illustrating an entire configuration of an endoscope system according to a first embodiment.

FIG. 1 is a diagram schematically illustrating an entire configuration of an endoscope system according to a first embodiment of the present invention. As illustrated in FIG. 1, an endoscope device 1 includes an endoscope 2, a universal cord 6, a connector 7, a light source device 9, a processor (control device) 10, and a display device 13.

The endoscope 2 captures an in-vivo image of a subject by inserting an insertion portion 4 into a body cavity of a subject and outputs an imaging signal. A cable bundle in the universal cord 6 is extended to a distal end of the insertion portion 4 of the endoscope 2 and connected to an imaging device provided in a distal end portion 31 of the insertion portion 4.

The connector 7 is provided to a proximal end of the universal cord 6, connected to the light source device 9 and the processor 10, performs specified signal processing on an imaging signal outputted from the imaging device in the distal end portion 31 connected with the universal cord 6, and analog-digital converts (A/D converts) the imaging signal to output the imaging signal as an image signal.

Pulse-shaped white light emitted from the light source device 9 becomes irradiation light with which an object is irradiated from the distal end of the insertion portion 4 of the endoscope 2 through the connector 7 and the universal cord 6. The light source device 9 is configured by using, for example, a white LED.

The processor 10 performs specified image processing on the image signal outputted from the connector 7 and controls the entire endoscope device 1. The display device 13 displays the image signal processed by the processor 10.

An operating unit 5 provided with various buttons and knobs for operating endoscope functions is connected to the proximal end of the insertion portion 4 of the endoscope 2. The operating unit 5 is provided with a treatment tool insertion opening 17 from which treatment tools such as an in-vivo forceps, an electrical scalpel, and an inspection probe are inserted into a body cavity of the subject.

The insertion portion 4 includes the distal end portion 31 provided with the imaging device, a bending portion 32 which can be bent in a plurality of directions and is connected to the proximal end of the distal end portion 31, and a flexible tube portion 33 connected to the proximal end of the bending portion 32. The bending portion 32 is bent by an operation of a bending operation knob provided in the operating unit 5 and can be bent in, for example, four directions of up, down, left, and right, following pulling and relaxing actions of a bending wire inserted into the insertion portion 4.

A light guide handle (not illustrated in the drawings) that transmits illumination light from the light source device 9 is arranged in the endoscope 2 and an illumination lens (not illustrated in the drawings) is arranged at an emitting end of the illumination light transmitted by the light guide handle. The illumination lens is provided at the distal end portion 31 of the insertion portion 4 and the subject is irradiated with the illumination light.

Figure 2:
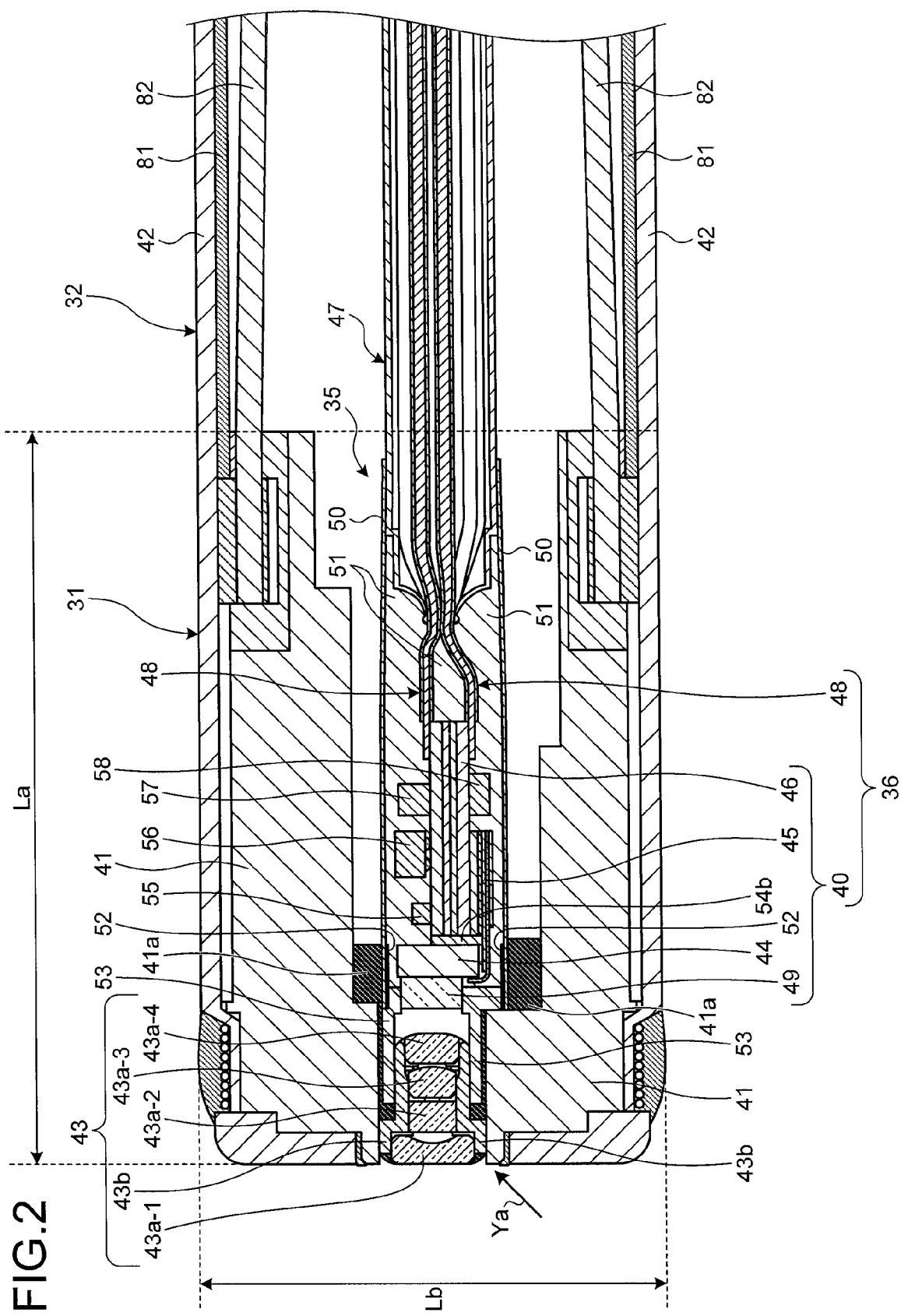
FIG. 2 is a partial cross-sectional view of a distal end of an endoscope illustrated in FIG. 1.

Next, a configuration of the distal end portion 31 of the endoscope 2 will be described in detail. FIG. 2 is a partial cross-sectional view of the distal end of the endoscope 2. FIG. 2 is a cross-sectional view taken along a surface which is orthogonal to a substrate surface of an imaging unit provided in the distal end portion 31 of the endoscope 2 and which is in parallel with an optical axis direction of the imaging unit.

FIG. 2 illustrates the distal end portion 31 of the insertion portion 4 of the endoscope 2 and a part of the bending portion 32.

As illustrated in FIG. 2, the bending portion 32 can be bent in four directions of up, down, left, and right following pulling and relaxing actions of a bending wire 82 inserted into a bending tube 81 arranged inside a covering tube 42 described later. An imaging device 35 is provided inside the distal end portion 31 extended from the distal end of the bending portion 32.

The imaging device 35 includes a lens unit 43 and an imaging unit 36 arranged facing the proximal end of the lens unit 43. The imaging device 35 is attached to the inside of a distal end main body 41 with an adhesive 41a. The distal end main body 41 is formed of a rigid member for forming an inner space that houses the imaging device 35. A proximal end periphery of the distal end main body 41 is covered with a flexible covering tube 42. A member located on the proximal end side with respect to the distal end main body 41 is formed of a flexible member so that the bending portion 32 can bend. The rigid portion of the insertion portion 4 is the distal end portion 31 in which the distal end main body 41 is arranged. The length La of the rigid portion is from the distal end of the insertion portion 4 to the proximal end of the distal end portion main body 41. The length Lb corresponds to the outer diameter of the distal end of the insertion portion 4.

The lens unit 43 includes a plurality of objective lenses 43a-1 to 43a-4, a lens holder 43b that holds the objective lenses 43a-1 to 43a-4. The distal end of the lens holder 43b is inserted into the distal end main body 41 and fixed, so that the lens unit 43 is fixed to the distal end main body 41.

The imaging unit 36 includes a solid-state imaging element 44 such as CCD or CMOS having a light receiving face that receives light on its surface, a substrate 45 extending from the solid-state imaging element 44, a multi-layer substrate 46 on which electronic components 55 to 58 including a drive circuit of the solid-state imaging element 44 are mounted, an imaging module 40 including a glass lid 49 attached to the solid-state imaging element 44 so as to cover the light receiving face of the solid-state imaging element 44, and a plurality of signal cables 48 electrically connected to the solid-state imaging element 44 to drive the solid-state imaging element 44. The multi-layer substrate 46 has the electronic components 55 to 58 mounted thereon, so that the multi-layer substrate 46 functions as a mounting substrate in the claims. The distal end of each signal cable 48 is electrically and mechanically connected to a cable connection land (not illustrated) provided on the multi-layer substrate 46 and the substrate 45. The plurality of signal cables 48 are gathered into an electric cable bundle 47 and extend in the proximal end direction.

The proximal end of each signal cable 48 extends in the proximal end direction of the insertion portion 4. The electric cable bundle 47 is inserted and arranged in the insertion portion 4 and extended to the connector 7 through the operating unit 5 and the universal cord 6 illustrated in FIG. 1.

A subject image formed by the objective lenses 43a-1 to 43a-4 of the lens unit 43 is photoelectrically converted by the solid-state imaging element 44 arranged at an image forming position of the objective lenses 43a-1 to 43a-4 and converted into an imaging signal which is an electrical signal. The imaging signal is outputted to the processor 10 through the signal cables 48 connected to the substrate 45 and the multi-layer substrate 46 and the connector 7.

The solid-state imaging element 44 is attached to the substrate 45 and the multi-layer substrate 46 with an adhesive 54b. The solid-state imaging element 44, a connection portion between the solid-state imaging element 44 and the substrate 45, and a connection portion between the solid-state imaging element 44 and the multi-layer substrate 46 are covered by a reinforcing member 52 formed of a metallic material having a sleeve shape open at both ends. The reinforcing member 52 is placed away from the solid-state imaging element 44 and the substrate 45 in order to avoid influence of static electricity and disturbance noise flowing in from the outside as illustrated by an arrow Ya to the electronic components 55 to 58 on the substrate 45 and a wiring pattern (not illustrated in the drawings) on the substrate 45.

The peripheries of the imaging unit 36 and the distal end portion of the electric cable bundle 47 are covered by a heat shrinkable tube 50 to improve durability. In the heat shrinkable tube 50, gaps between components are filled with an adhesive resin 51. The outer circumferential surface of the reinforcing member 52 and the inner circumferential surface of a distal end portion of the heat shrinkable tube 50 are in contact with each other without a gap.

The outer circumferential surface of the glass lid 49 is fitted into the inner circumferential surface of a proximal end side of a solid-state imaging element holder 53, so that the solid-state imaging element holder 53 holds the solid-state imaging element 44 attached to the glass lid 49. The outer circumferential surface of a proximal end portion of the solid-state imaging element holder 53 is fitted into the inner circumferential surface of a distal end portion of the reinforcing member 52. The outer circumferential surface of a proximal end portion of the lens holder 43b is fitted to the inner circumferential surface of a distal end portion of the solid-state imaging element holder 53. In a state in which components are fitted to each other in this way, the outer circumferential surface of the lens holder 43b, the outer circumferential surface of the solid-state imaging element holder 53, and the outer circumferential surface of a distal end portion of the heat shrinkable tube 50 are fixed to the inner circumferential surface of a distal end portion of the distal end main body 41 by the adhesive 41a.

Figure 3:
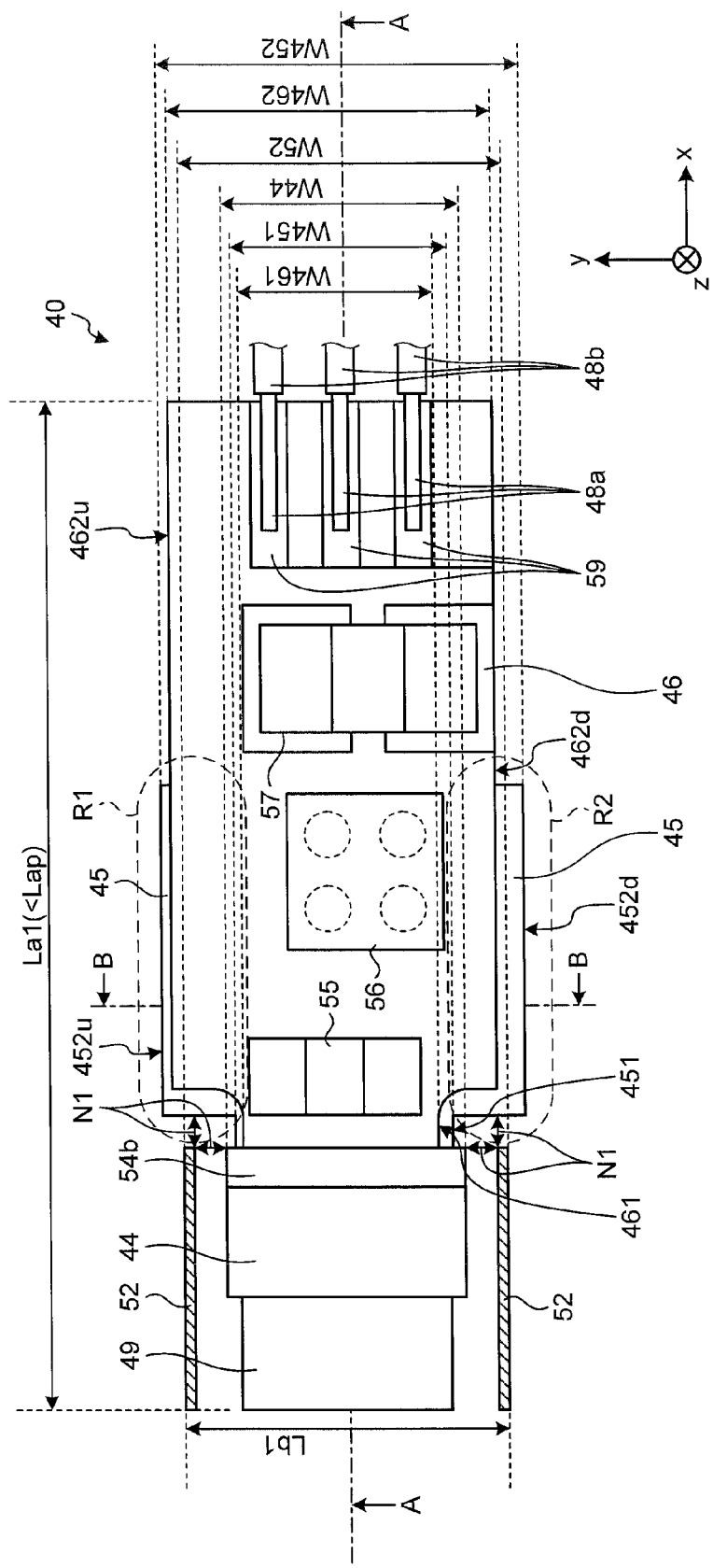
FIG. 3 is a plan view of an imaging module illustrated in FIG. 2.
Figure 4:
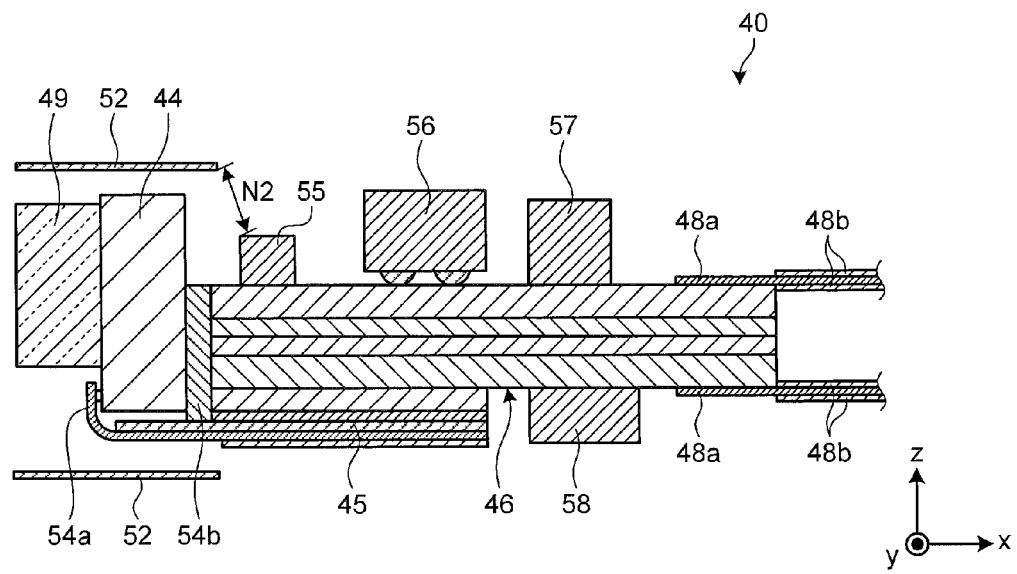
FIG. 4 is a cross-sectional view taken along line A-A in FIG. 3.
Figure 5:
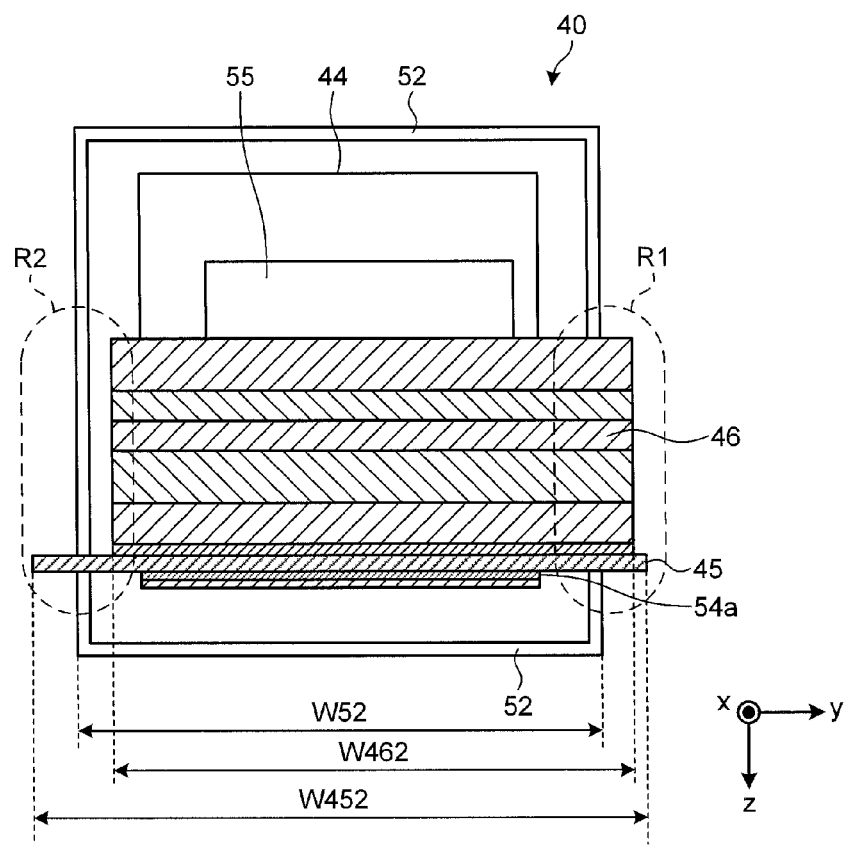
FIG. 5 is a cross-sectional view taken along line B-B in FIG. 3.

Next, the imaging module 40 will be described. FIG. 3 is a plan view of the imaging module 40 and a diagram of the imaging module 40 as seen from above the substrate 45. For the sake of description, FIG. 3 illustrates a state in which the reinforcing member 52 is cut off along a surface in parallel with a surface of the substrate 45. FIG. 4 is a cross-sectional view taken along line A-A in FIG. 3 and a cross-sectional view of the imaging module 40 taken along a surface which is perpendicular to the surface of the substrate 45 and in parallel with an optical axis direction of the solid-state imaging element 44. FIG. 5 is a cross-sectional view taken along line B-B in FIG. 3 and a cross-sectional view of the imaging module 40 taken along a vertical plane to an optical axis direction of the solid-state imaging element 44. In FIGS. 3 to 5, an axis corresponding to the optical axis direction of the solid-state imaging element 44 is defined as an x axis. Further, an axis corresponding to a direction in parallel with the surface of the substrate 45 and perpendicular to the optical axis direction of the solid-state imaging element 44 is defined as a y axis. Further, in FIGS. 3 to 5, an axis corresponding to a direction in parallel with a vertical plane to the surface of the substrate 45 and orthogonal to the optical axis direction of the solid-state imaging element 44 is defined as a z axis. In FIGS. 3 to 5, the adhesive resin 51 is omitted.

As illustrated in FIGS. 3 to 5, in the imaging module 40, a lower electrode (not illustrated in the drawings) of the solid-state imaging element 44 and an electrode (not illustrated in the drawings) of the back surface of the substrate 45 are electrically connected by an inner lead 54a. The inner lead 54a is bent to an angle of approximately 90° at the distal end of the substrate 45 and fixed to the solid-state imaging element 44 and the substrate 45 by an adhesive.

The substrate 45 is a rigid substrate and is connected and fixed to the solid-state imaging element 44 at its distal end portion facing the solid-state imaging element 44. The rear end portion of the substrate 45 is extended and arranged in the optical axis direction of the solid-state imaging element 44. The rigid multi-layer substrate 46 in which a plurality of layers are provided is formed on the surface of the substrate 45. In the example of FIG. 4, five layers are provided as the multi-layer substrate 46. A side surface of the distal end of the multi-layer substrate 46 is connected and fixed to the back surface of the solid-state imaging element 44 by the adhesive 54b and the rear end portion of the multi-layer substrate 46 is extended and arranged in the optical axis direction of the solid-state imaging element 44. The rear end portion of the multi-layer substrate 46 is more extended in the optical axis direction of the solid-state imaging element 44 than the rear end of the substrate 45. The solid-state imaging element 44 is attached to a part of the upper surface of the substrate 45 by the adhesive 54b on the back surface of the solid-state imaging element 44. The substrate 45 electrically connects the multi-layer substrate 46, which is a mounting substrate, with the solid-state imaging element 44, so that the substrate 45 functions as a connection substrate in the claims.

In the reinforcing member 52, an opening direction of a hollow portion is in parallel with the optical axis. The reinforcing member 52 protects the solid-state imaging element 44, a connection portion 451 between the solid-state imaging element 44 and the substrate 45 described later, and a connection portion 461 between the solid-state imaging element 44 and the multi-layer substrate 46 described later from an external force by covering them along the optical axis direction. The inner circumferential surface of the reinforcing member 52 is located at a position away from the solid-state imaging element 44, the substrate 45, the multi-layer substrate 46, and the electronic components 55 to 58 by a certain distance N1 or more in order to avoid influence of static electricity and disturbance noise to the electronic components 55 to 58 on the substrate 45 and a wiring pattern on the substrate 45. The distance N1 is set based on electrostatic resistance and disturbance noise tolerance.

The electronic components 55 to 57 are mounted on a surface of an uppermost layer of the multi-layer substrate 46. The electronic component 58 is mounted on a back surface of a second layer of the multi-layer substrate 46. In the first embodiment, the electronic component 55 which is the lowest of the plurality of electronic components 55 to 57 is arranged at a position closest to the solid-state imaging element 44, so that the distance between the inner circumferential surface of the reinforcing member 52 and the electronic component 55 is increased to a distance N2 (≥N1) by which the electrostatic resistance and the disturbance noise tolerance can be ensured.

On the multi-layer substrate 46, a cable connection land 59 to which a conductor 48a of the distal end of the signal cable 48 is electrically and mechanically connected is provided. The conductor 48a is connected to the multi-layer substrate 46 by being soldered to the cable connection land 59. The conductor 48a is covered by a covering body 48b except for the distal end that is connected to the cable connection land 59.

In the example of FIG. 3, three cable connection lands 59 are provided on the surface of the uppermost layer of the multi-layer substrate 46. The cable connection land is also provided on the back surface of the second layer of the multi-layer substrate 46 (not illustrated in the drawings). All of the cable connection lands 59 are provided on the proximal end side with respect to the electronic components 55 to 58 opposite to the solid-state imaging element 44 along the optical axis direction. When the cable connection lands are located closer to the solid-state imaging element than the electronic components, the signal cables interfere with each other on the electronic components. As a result, the size of the outer shape of the entire imaging unit may increase. In the first embodiment, the cable connection lands 59 are provided on the proximal end side, so that the signal cables 48 do not interfere with each other on the electronic components 55 to 58. Therefore, the size of the outer shape does not increase due to the interference between the signal cables 48. When a plurality of cable connection lands 59 are provided on the same land surface, the plurality of cable connection lands 59 provided on the land surface are provided to be positioned and aligned on the same straight line in parallel with the y axis.

Here, as illustrated in FIG. 3, the substrate 45 has the connection portion 451 that is connected and fixed to the solid-state imaging element 44 on its distal end side facing the solid-state imaging element 44 and has protrusion portions 452u and 452d on the rear end side with respect to the connection portion 451.

The connection portion 451 of the substrate 45 is located inside an imaging element projection area that is a projection area where the solid-state imaging element 44 is projected in the x axis direction which is the optical axis direction. The connection portion 451 of the substrate 45 includes a portion that is connected to the back surface of the solid-state imaging element 44 by the adhesive 54b. The connection portion 451 is located inside the imaging element projection area where the solid-state imaging element 44 is projected in the optical axis direction, so that when the connection portion 451 is seen in a plan view in the z axis direction as in FIG. 3, the width W451 in the y axis direction of the projection area in the x axis direction of the connection portion 451 of the substrate 45 is smaller than the width W44 in the y axis direction of the imaging element projection area.

The protrusion portions 452u and 452d of the substrate 45 are formed so as to protrude in the y axis direction from a reinforcing member projection area where the outer circumference of the reinforcing member 52 is projected in the x axis direction which is the optical axis direction. Therefore, when the substrate 45 is seen in a plan view in the z axis direction, the width W452 in the y axis direction of a projection area where the rear end side of the substrate 45 including the protrusion portions 452u and 452d is projected in the x axis direction is greater than the outer diameter W52 in the y axis direction of the reinforcing member 52.

In the same manner as the substrate 45, as illustrated in FIG. 3, the multi-layer substrate 46 has the connection portion 461 that is connected and fixed to the back surface of the solid-state imaging element 44 on its distal end side facing the solid-state imaging element 44 and has protrusion portions 462u and 462d on the rear end side with respect to the connection portion 461.

The connection portion 461 of the multi-layer substrate 46 is located inside the imaging element projection area described above. Therefore, when the connection portion 461 is seen in a plan view in the z axis direction as in FIG. 3, the width W461 in the y axis direction of the projection area in the x axis direction of the connection portion 461 of the multi-layer substrate 46 is smaller than the width W44 in the y axis direction of the imaging element projection area.

The protrusion portions 462u and 462d of the multi-layer substrate 46 protrude to the outside of the imaging element projection area in a state in which the protrusion portions 462u and 462d are away from the rear end of the reinforcing member 52 by a specified distance N1 or more. Specifically, when the protrusion portions 462u and 462d are seen in a plan view in the z axis direction as in FIG. 3, the protrusion portions 462u and 462d protrude upward and downward, respectively, in the y axis direction in an area in the optical axis direction of the reinforcing member 52 in a state in which the protrusion portions 462u and 462d are away from the rear end of the reinforcing member 52 by a specified distance N1 or more. Since there are the protrusion portions 462u and 462d, when the multi-layer substrate 46 is seen in a plan view in the z axis direction, the width W462 in the y axis direction of a projection area where the rear end side of the multi-layer substrate 46 is projected in the x axis direction is greater than the width W461 in the y axis direction of a projection area where the connection portion 461 of the multi-layer substrate 46 is projected in the x axis direction. In the example of FIG. 3, the protrusion portion 462u is formed to protrude in the y axis direction from the reinforcing member projection area described above.

Figure 6:
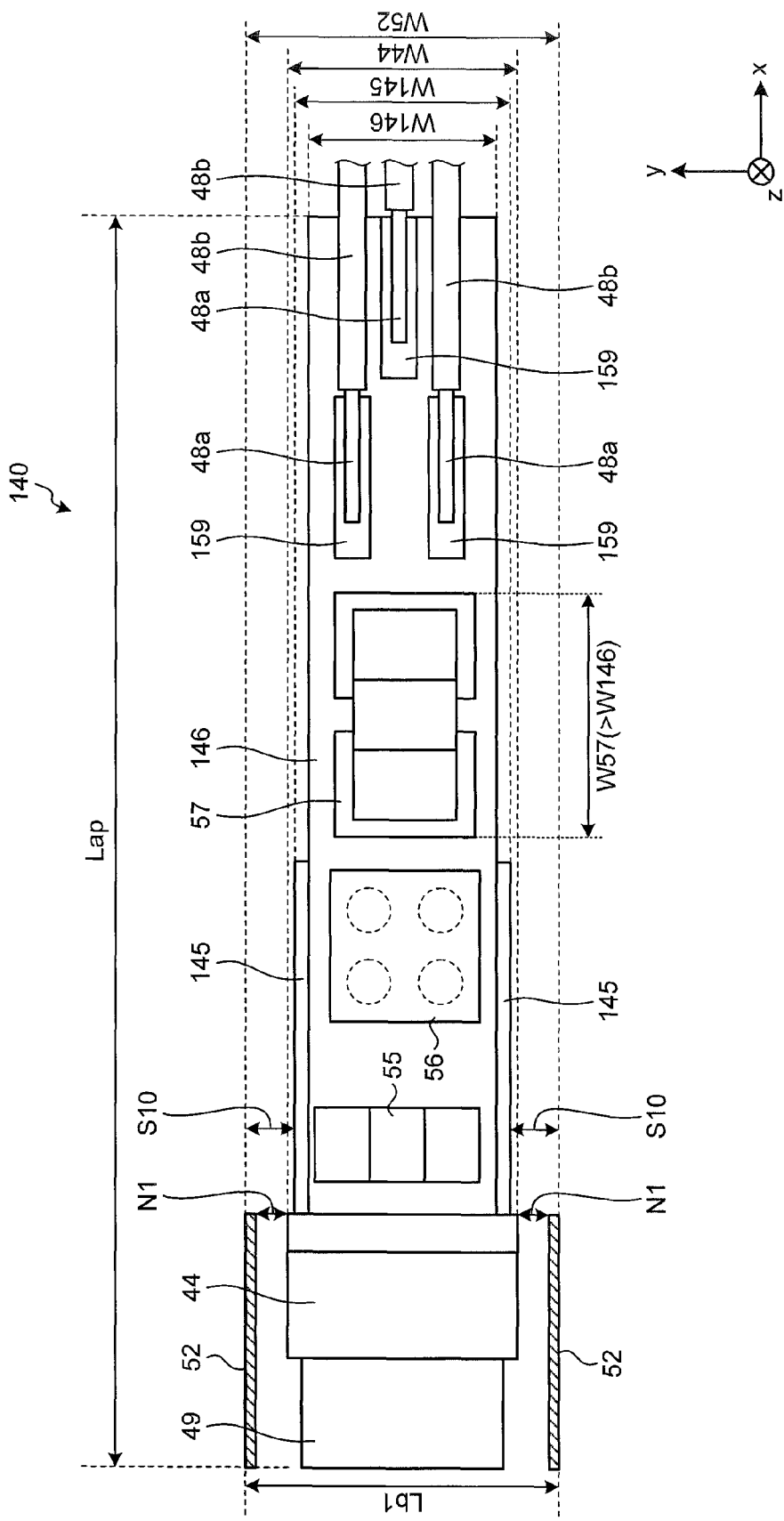
FIG. 6 is a plan view of an imaging module according to a conventional technique.

Here, an imaging module according to a conventional technique will be described. FIG. 6 is a plan view of an imaging module according to a conventional technique and is a diagram of a surface of a substrate seen from above. In a conventional imaging module 140 illustrated in FIG. 6, the solid-state imaging element 44 is arranged away from the inner circumferential surface of the reinforcing member 52 by a certain distance N1 in order to ensure the electrostatic resistance and the disturbance noise tolerance. In the same manner, for both of a substrate 145 and a multi-layer substrate 146 which are formed into a rectangular shape, the widths of the connection portions are set such that an end portion of each substrate is located away from the inner circumferential surface of the reinforcing member 52 by the distance N1 or more in order to ensure the electrostatic resistance and the disturbance noise tolerance. Both of the substrate 145 and the multi-layer substrate 146 extend in the x axis direction while maintaining the widths. In a conventional configuration, in a plan view seen in the z axis direction, the components of the imaging unit including the electronic components and the signal cables in addition to the substrate 145 and the multi-layer substrate 146 are arranged in a projection area where the solid-state imaging element 44 is projected in the x axis direction. Therefore, when the substrate 145 is seen in a plan view in the z axis direction, the substrate 145 is formed into a rectangular shape so that the width W145 in the y axis direction of a projection area where the substrate 145 is projected in the x axis direction is smaller than the width W44 in the y axis direction of the solid-state imaging element 44. In the same manner as the substrate 145, the multi-layer substrate 146 is formed into a rectangular shape so that the width W146 in the y axis direction of a projection area where the multi-layer substrate 146 is projected in the x axis direction is smaller than the width W44.

Reference will be made to a case in which the electronic component 57 that requires a width with a length of W57 (>W44) including a connection land is mounted on the multi-layer substrate 146. In the case of FIG. 6, the width W146 in the y axis direction of the multi-layer substrate 146 is shorter than the length W57. Therefore, the electronic component 57 cannot be mounted so that the short side direction of the electronic component 57 is in parallel with the x axis, and thus the electronic component 57 has to be mounted so that the longitudinal direction of the electronic component 57 is in parallel with the x axis as illustrated in FIG. 6. Therefore, to place the electronic components 55 to 57 including the electronic component 57 on the multi-layer substrate 146, the multi-layer substrate 146 has to be extended in the x axis direction. Therefore, the length Lap in the x axis direction of the imaging module 140 becomes longer than that in a case in which the electronic component 57 is mounted so that the longitudinal direction of the electronic component 57 is in parallel with the y axis.

Further, in a conventional imaging module, the widths W145 and W146 in the y axis direction of the substrate 145 and the multi-layer substrate 146 are small, so that all of a plurality of connection lands 159 cannot be arranged on the same straight line in parallel with the y axis. Therefore, as illustrated in FIG. 6, the plurality of connection lands 159 may have to be arranged by shifting the connection lands 159 in the x axis direction, so that the length in the x axis direction of the multi-layer substrate 146 becomes longer. As described above, in the conventional configuration, the multi-layer substrate has to be long in the x axis direction, so that the length in the x axis direction of the distal end main body of the distal end of the insertion portion becomes long. Therefore, there is a limitation for shortening the length of the rigid portion of the distal end of the insertion portion.

On the other hand, in the multi-layer substrate 46 illustrated in FIG. 3, two protrusion portions 462u and 462d are formed on the rear end side with respect to the connection portion 461. In the same manner, in the substrate 45, two protrusion portions 452u and 452d are formed on the rear end side with respect to the connection portion 451. Therefore, the rear end portions of the substrate 45 and the multi-layer substrate 46 are largely extended in the y axis direction.

In this way, the multi-layer substrate 46 is extended in the y axis direction in a portion on the rear end side with respect to the connection portion 461. Therefore it is possible to mount the electronic component 57 on the multi-layer substrate 46 so that the longitudinal direction of the electronic component 57 is in parallel with the y axis without extending the multi-layer substrate 46 in the x axis direction. In other words, it is possible to mount the electronic component 57 on the multi-layer substrate 46 so that the short side direction of the electronic component 57 is in parallel with the x axis. The rear end portion of the multi-layer substrate 46 is extended in the y axis direction, so that all of the three cable connection lands 59 can be arranged to be positioned on the same straight line in parallel with the y axis. Therefore, it is possible to minimize the length in the x axis direction required for the cable connection lands 59.

Therefore, in the imaging module 40, if the outer diameter of the distal end portion of the imaging module is the same as the diameter Lb1 of the conventional imaging module 140 illustrated in FIG. 6, the length La1 in the x axis direction of the imaging module 40 can be smaller than the length Lap in the x axis direction of the conventional imaging module 140.

The substrate 45 and the connection portions 451 and 461 of the multi-layer substrate 46 as illustrated in FIG. 3 are arranged within the imaging element projection area and maintain a state in which the substrate 45 and the connection portions 451 and 461 are away from the inner circumferential surface of the reinforcing member 52 by the distance N1 in the same manner as the solid-state imaging element 44. Therefore, in the imaging module 40, all of the solid-state imaging element 44, the substrate 45, the multi-layer substrate 46, and the electronic components 55 to 58 are positioned away from the reinforcing member 52 by a certain distance N1 or more by which the electrostatic resistance and the disturbance noise tolerance can be ensured. Therefore, it is possible to ensure the electrostatic resistance and the disturbance noise tolerance.

Further, as illustrated in an area S10 in FIG. 6, conventionally, an area which is an area in the optical axis direction of the reinforcing member 52 and where the protrusion portions 452u and 452d of the substrate 45 and the protrusion portions 462u and 462d of the multi-layer substrate 46 are located is a dead space in which no member is arranged and which is only filled with an adhesive resin. Therefore, even when the protrusion portions 462u, 462d, 452u, and 452d are provided to the multi-layer substrate 46 and the substrate 45, it does not affect the arrangements and the operations of other members.

In this way, in the first embodiment, the rear end portions of the substrate 45 and the multi-layer substrate 46 are extended by effectively using a space in the optical axis direction of the reinforcing member 52, which is conventionally a dead space, so that it is possible to arrange the electronic components 55 to 58 and the cable connection lands 59 without extending the multi-layer substrate 46 in the optical axis direction.

Figure 7:
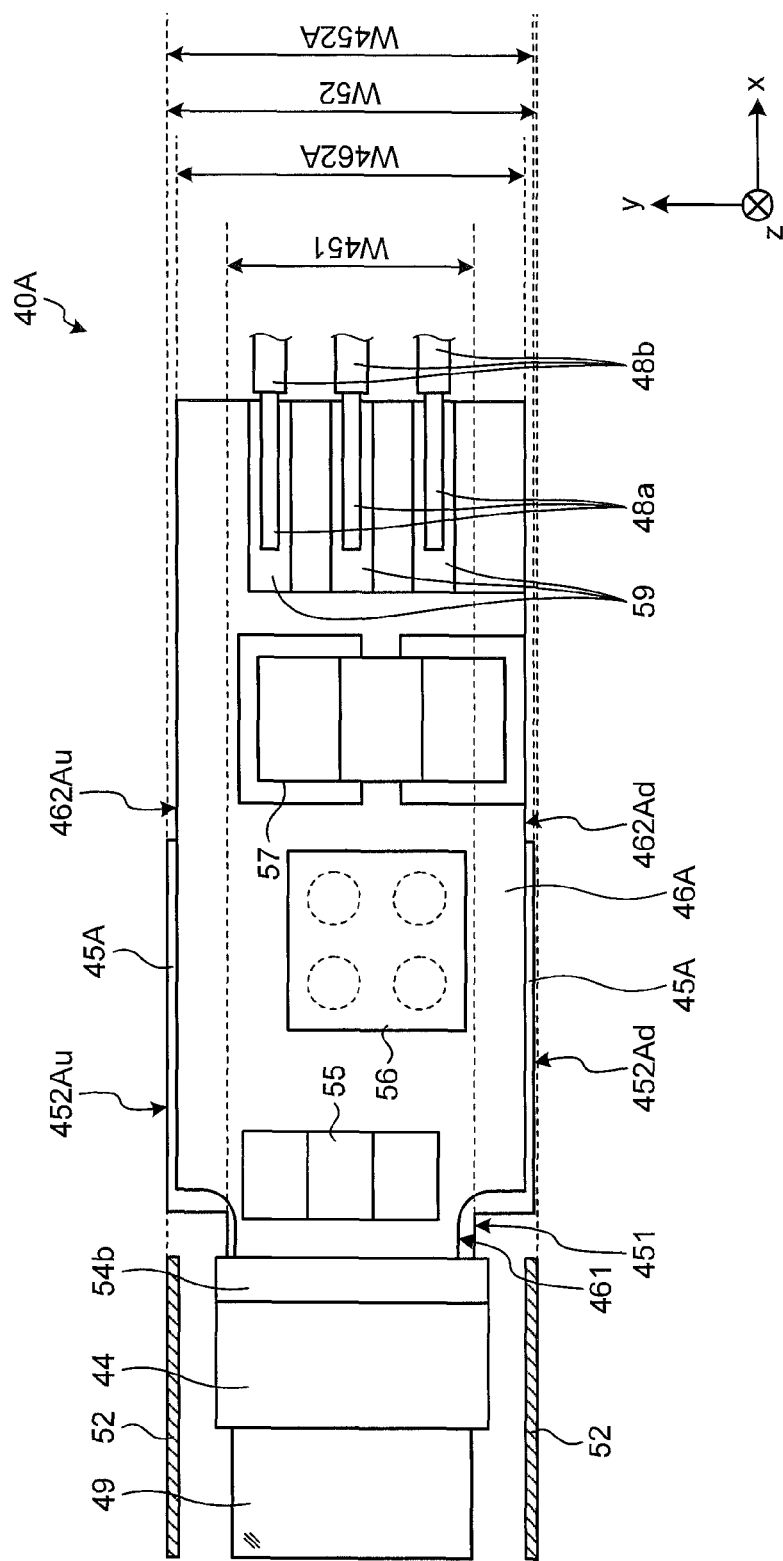
FIG. 7 is a plan view illustrating another example of the imaging module illustrated in FIG. 2.

In the first embodiment, as in an imaging module 40A illustrated in FIG. 7, protrusion portions 462Au and 462Ad of a multi-layer substrate 46A may be positioned inside the reinforcing member projection area described above. In the same manner, protrusion portions 452Au and 452Ad of a substrate 45A may be positioned inside the reinforcing member projection area. Therefore, in the imaging module 40A, when the imaging module 40A is seen in a plan view in the z axis direction, the width W462A in the y axis direction of a projection area where the rear end side of the multi-layer substrate 46A is projected in the x axis direction and the width W452A in the y axis direction of a projection area where the rear end side of the substrate 45A is projected in the x axis direction are smaller than or equal to the outer diameter W52 of the reinforcing member 52. Further, when the electronic components 55 to 58 mounted on the imaging module 40A and the signal cables 48 connected to the imaging module 40A are arranged inside the reinforcing member projection area, the heat shrinkable tube 50 covers the entire imaging unit while maintaining substantially the same inner diameter as the outer diameter W52 of the reinforcing member 52 regardless of the shapes of the substrate 45A and the multi-layer substrate 46A. Therefore, in this case, the outer diameter of the imaging unit including the imaging module 40A is substantially the same from the distal end to the rear end along the optical axis direction, so that components can be easily installed.

Figure 8:
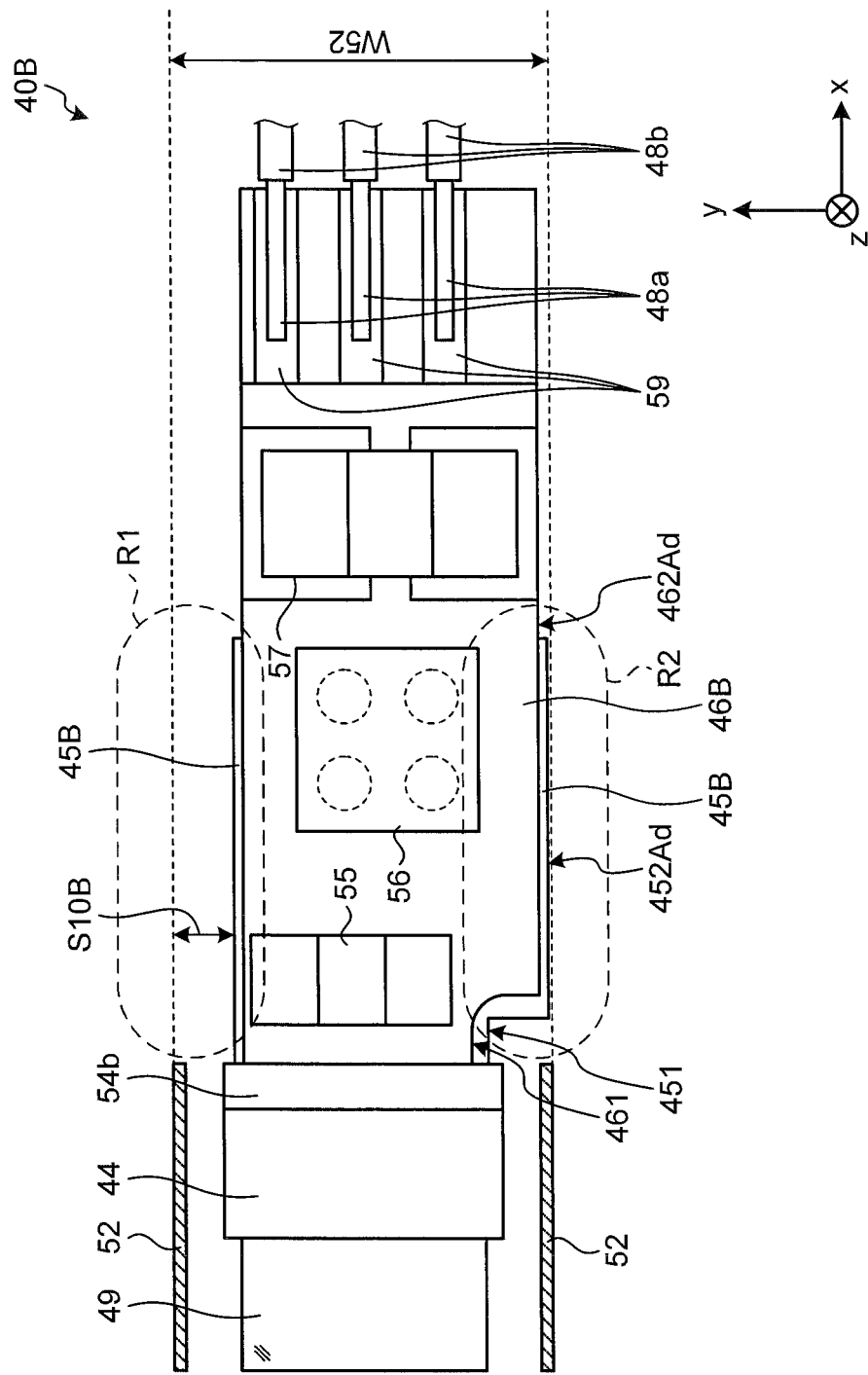
FIG. 8 is a plan view illustrating another example of the imaging module illustrated in FIG. 2.

As illustrated in an imaging module 40B in FIG. 8, the protrusion portions 452Ad and 462Ad are provided in only the area R2 located lower in the y axis direction of a substrate 45B and a multi-layer substrate 46B, and a space S10B including the other area R1 including no protrusion portion may be used for other members.

Figure 9:
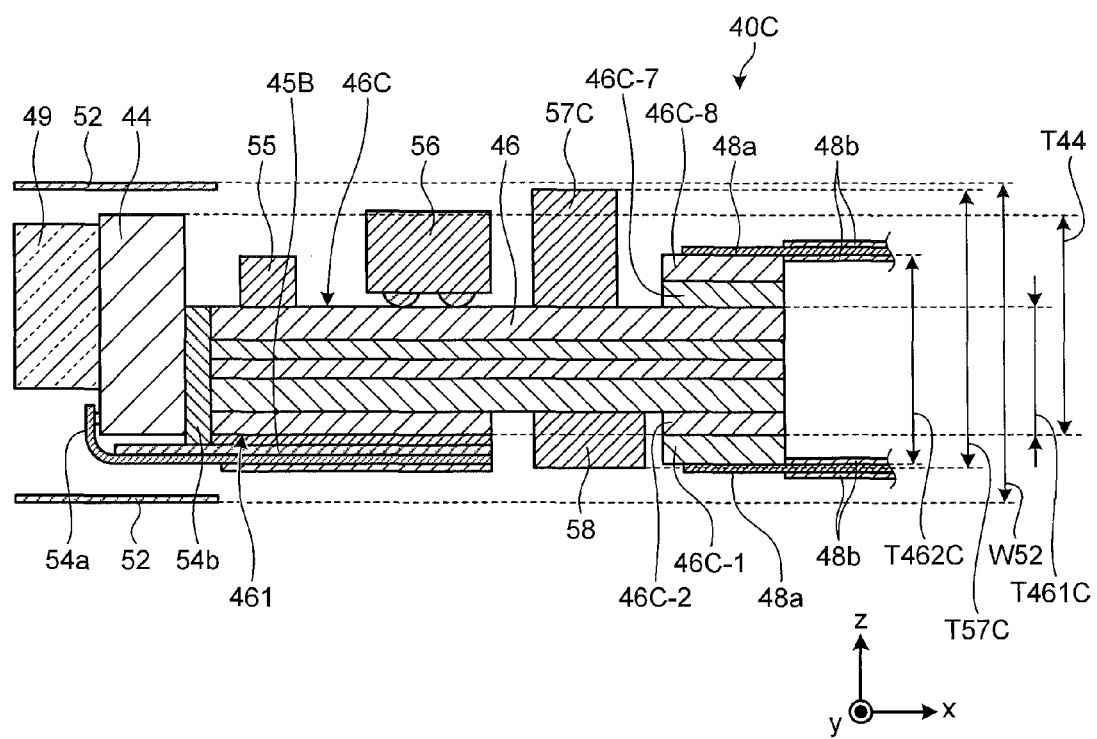
FIG. 9 is a partial cross-sectional view illustrating another example of the imaging module illustrated in FIG. 2.

In addition to extending the rear end portions of the substrate and the multi-layer substrate along the y axis direction as in the imaging modules 40, 40A, and 40B illustrated in FIGS. 3, 7, and 8, as illustrated in an imaging module 40C in FIG. 9, protrusion portions may be formed by thickening the rear end portion of the multi-layer substrate 46 in the z axis direction that is a lamination direction of the multi-layer substrate 46. In a multi-layer substrate 46C constituting the imaging module 40C, a seventh layer 46C-7 and an eighth layer 46C-8 are formed on the upper surface of the rear end portion of the multi-layer substrate 46 and a first layer 46C-1 and a second layer 46C-2 are formed on the lower surface of the rear end portion of the multi-layer substrate 46, so that the rear end portion is thicker than the distal end portion. Therefore, as illustrated in FIG. 9, when a cross-section of the imaging module 40C taken along a surface which is perpendicular to the surface of the substrate 45 and in parallel with the optical axis direction of the solid-state imaging element 44 is seen in a plan view in the y axis direction, the first layer 46C-1 of the multi-layer substrate 46C becomes a protrusion portion that protrudes downward in the z axis direction from the imaging element projection area described above. In this case, the size T462C in the z axis direction of a projection area in the x axis direction of the rear end side of the multi-layer substrate 46C is greater than the size T461C of a projection area in the x axis direction of the connection portion 461 on the distal end side of the multi-layer substrate 46C, so that it is possible to secure a wiring space in the rear end portion of the multi-layer substrate 46C. Further, when the mounting substrate includes electronic components 55, 56, 57C, and 58 in addition to the multi-layer substrate 46C, it is possible to configure the mounting substrate so that a portion which is located in a rear end portion of the multi-layer substrate 46C and which includes the electronic components 57C and 58 is projected in the x axis direction and the size T570 in the z axis direction of the projection area is greater than the size T44 in the z axis direction of the imaging element projection area. The size T57C may be set to smaller than or equal to the outer diameter W52 of the reinforcing member 52 and the outer diameter of the imaging unit including the imaging module 40C may be set to substantially the same diameter from the distal end to the rear end. As described above, in the first embodiment, when the protrusion portion provided in the rear end side of the multi-layer substrate is formed to protrude to the outside of the imaging element projection area, the protrusion portion may protrude in any direction of the z axis direction and the y axis direction.

SECOND EMBODIMENT

Figure 10:
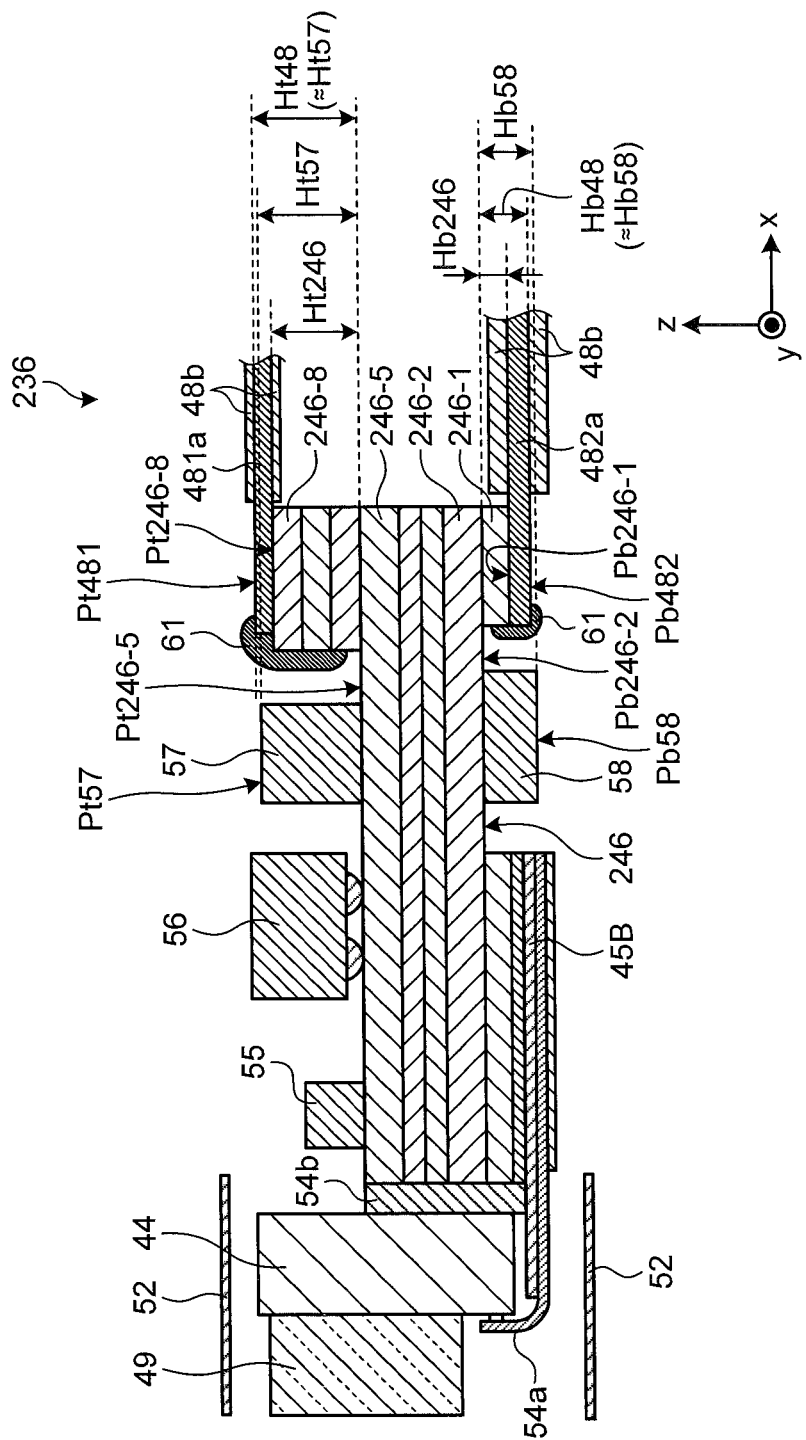
FIG. 10 is a partial cross-sectional view of an imaging unit according to a second embodiment.

Next, a second embodiment will be described. FIG. 10 is a partial cross-sectional view illustrating an imaging unit according to the second embodiment. FIG. 10 is a cross-sectional view of an imaging unit taken along a surface perpendicular to a surface of a light receiving area of an imaging element included in the imaging unit according to the second embodiment.

As illustrated in FIG. 10, an imaging unit 236 according to the second embodiment includes a multi-layer substrate 246 in which eight layers are provided on the proximal end side. On an upper side and back side of the multi-layer substrate, the electronic components 55 to 58 are mounted and cable connection lands (not illustrated in the drawings) to which conductors 481a and 482a of the signal cables 48 are connected are provided on the proximal end side.

As illustrated in FIG. 10, the electronic components 55 to 57 are mounted on an upper surface Pt246-5 of a fifth layer 246-5 of the multi-layer substrate 246. On an upper surface Pt246-8 of an uppermost eighth layer 246-8 of the multi-layer substrate 246, a cable connection land to which the conductor 481a of the signal cable 48 is connected is provided. Therefore, the upper surface Pt246-8 which is a land surface on which the cable connection land is provided is a surface different from the upper surface Pt246-5 which is a mounting surface of the electronic components 55 to 57. The upper surface Pt246-8 which is the land surface corresponds to a surface located upward away in the z axis direction from the upper surface Pt246-5 which is the mounting surface by a distance corresponding to three layers. Therefore, the upper surface Pt246-8 which is the land surface is provided at a position vertically away from the upper surface Pt246-5 which is the mounting surface by the level distance.

The height of the upper surface of the conductor 481a is set to equal to the height of the upper surface of the electronic component 57 mounted closest to the signal cable having the conductor 481a. In the case of FIG. 10, the thickness Ht246 of the multi-layer substrate 246 from the mounting surface Pt246-5 is set such that the height of the upper surface Pt57 of the electronic component 57 mounted closest to the signal cable having the conductor 481a is substantially equal to the height of the upper surface Pt481 of the conductor 481a connected to the cable connection land on the eighth layer 246-8. In other words, the thickness Ht246 of the multi-layer substrate 246 from the mounting surface Pt246-5 is set such that the distance Ht57 between the mounting surface Pt246-5 and the upper surface Pt57 of the electronic component 57 in the z axis direction is nearly equal to the distance Ht48 between the mounting surface Pt246-5 and the upper surface Pt481 of the conductor 481a in the z axis direction.

The same goes for a case in which the electronic components are mounted on the back surface of the multi-layer substrate 246. As an example of this case, the electronic component 58 mounted on a lower surface Pb246-2 of a second layer 246-2 of the multi-layer substrate 246 and the conductor 482a of the signal cable connected to the connection land on a lower surface Pb246-1 of a first layer 246-1 of the multi-layer substrate 246 will be described. Also in this case, the thickness Hb246 of the multi-layer substrate 246 from the mounting surface Pb246-2 is set such that the height of the lower surface Pb58 of the electronic component 58 mounted closest to the signal cable having the conductor 482a is substantially equal to the height of the lower surface Pb482 of the first layer 246-1 which is the land surface. In other words, the thickness Hb246 of the multi-layer substrate 246 from the mounting surface Pb246-2 is set such that the distance Hb58 between the mounting surface Pb246-2 and the lower surface Pb58 of the electronic component 58 in the z axis direction is substantially equal to the distance Hb48 between the mounting surface Pb246-2 and the lower surface Pb482 of the conductor 482a in the z axis direction. As described above, in the second embodiment, the distance between a non-contact surface opposite to a land surface of the cable connection land of the signal cable 48 and the mounting surface of the electronic components in the vertical direction to the mounting surface is set to equal to the distance between the electronic component mounted closest to the signal cable and the mounting surface in the vertical direction to the mounting surface. The distance between the non-contact surface opposite to the land surface of the cable connection land of the signal cable 48 and the mounting surface of the electronic components in the vertical direction to the mounting surface and the distance between the electronic component mounted closest to the signal cable and the mounting surface in the vertical direction to the mounting surface need not be completely equal to each other, but may be within an allowable error range considering various variations such as variation of thickness of the multi-layer substrate, variation of the size of each member, variation of mounting accuracy, variation of the amount of solder applied per time, and the amount of deviation of a soldering iron that comes into contact.

In the conventional configuration in which the cable connection land and the mounting surface are provided on the same plane, to prevent a clearance between an electronic component and the cable connection land from being short-circuited due to solder flowing from the cable connection land to the mounting surface, the clearance between the electronic component and the cable connection land is required to be large. As a result, in the conventional configuration, the length in the x axis direction of the multi-layer substrate has to be long, so that there is a problem that the length of the rigid portion of the distal end of the insertion portion of the endoscope is long.

Figure 11:
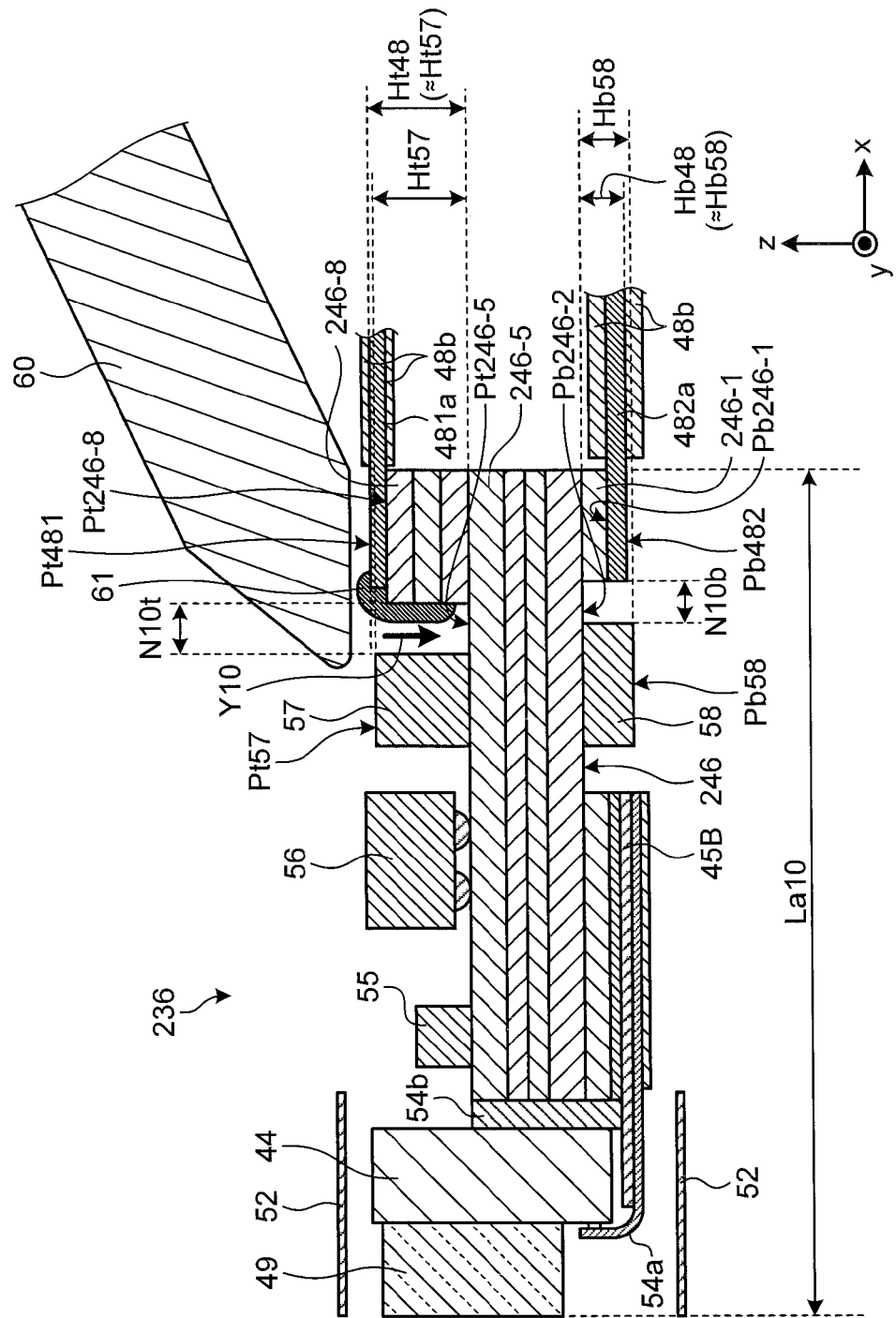
FIG. 11 is diagram for explaining soldering of the imaging unit illustrated in FIG. 10.

On the other hand, in the imaging unit 236 in the second embodiment, the number of layers of the multi-layer substrate is increased in an area where the cable connection land is placed, so that a level difference is formed between the electronic component and the cable connection land and a long distance is provided between the mounting surface and the cable connection land. Therefore, in the imaging unit 236, even when solder 61 flows out as illustrated by an arrow Y10 in FIG. 11, the distance for the solder 61 to reach the electronic component is long, so that a short-circuit between the conductor 481a connected to the cable connection land and the electronic component 57 is more difficult to occur than in the conventional configuration.

In the conventional configuration in which the cable connection land and the mounting surface are provided on the same surface, a distal end of a soldering iron comes into contact with the electronic component in a soldering process of the signal cable, so that the clearance between the electronic component and the cable connection land is required to be large.

On the other hand, in the imaging unit 236 in the second embodiment, the number of layers on the proximal end side of the multi-layer substrate 246 is increased and the height of the land surface of the cable connection land is raised so that the height of the upper surface Pt481 of the conductor 481a is the same as the height of the upper surface Pt57 of the electronic component 57. As a result, in the imaging unit 236, there is not the electronic component 57 in a distal end direction of a soldering iron 60, so that the soldering iron 60 does not hit the electronic component 57.

Therefore, in the imaging unit 236, even when a distance N10t between the electronic component 57 and an end portion of the eighth layer 246-8 on which the cable connection land is formed is small, a short-circuit due to flowing out of the solder 61 and an interference of the soldering iron 60 do not occur. In the same manner, on the back surface, even when a distance N10b between the electronic component 58 and an end portion of the first layer 246-1 on which the cable connection land is formed is small, the height of the lower surface Pb482 of the conductor 482a is substantially the same as the height of the lower surface Pb58 of the electronic component 58 and the distance between the mounting surface and the cable connection land is long, so that a short-circuit due to flowing out of the solder 61 and an interference of the soldering iron 60 do not occur. Therefore, in the second embodiment, it is possible to reduce a length La10 of the rigid portion of the imaging unit 236 and reduce the size of the imaging unit 236 itself, and accordingly, it is possible to reduce the length of the rigid portion of the distal end of the insertion portion of the endoscope.

Figure 12:
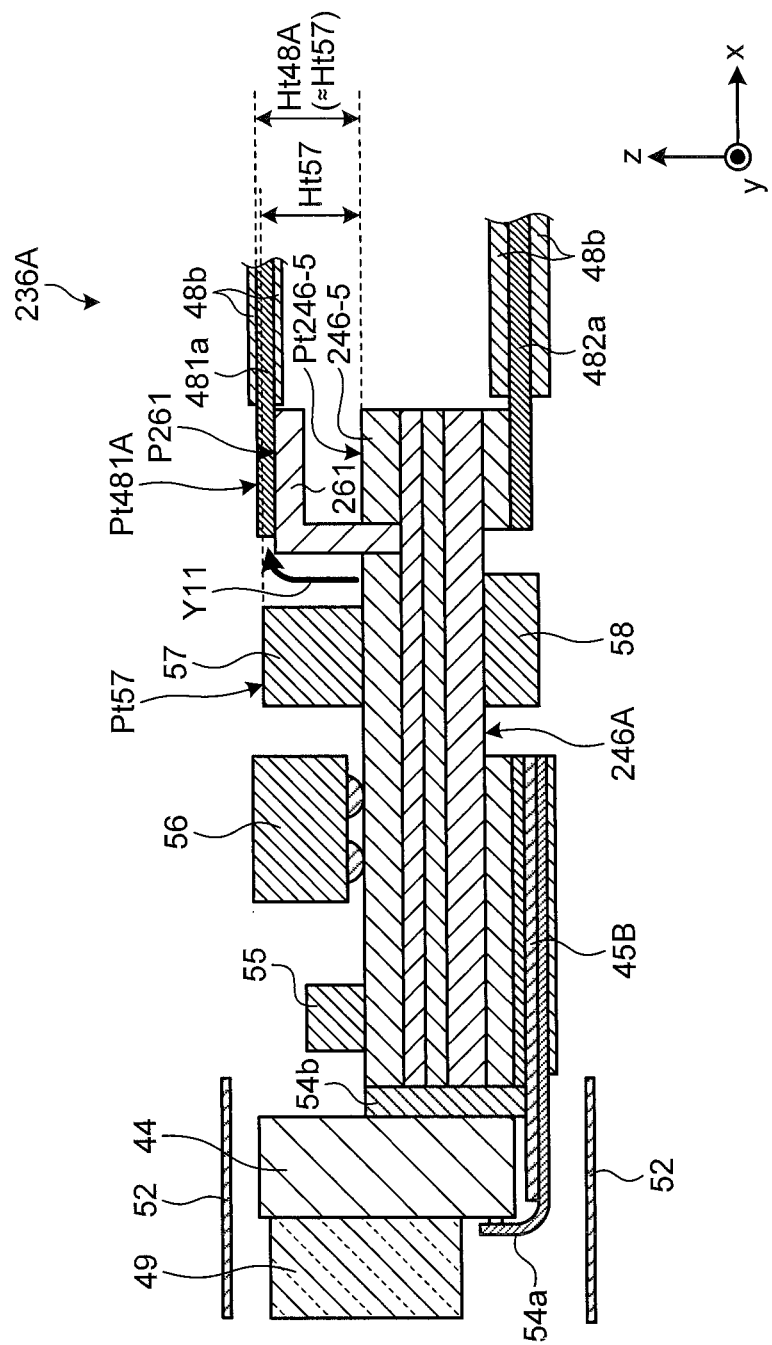
FIG. 12 is a partial cross-sectional view of another example of the imaging unit according to the second embodiment.

In the second embodiment, as in an imaging unit 236A illustrated in FIG. 12, in a multi-layer substrate 246A, a metallic component 261 is provided on the upper surface Pt246-5 of the fifth layer 246-5 which is the mounting surface and a cable connection land is provided on the upper surface P261 of the metallic component 261, so that the height Ht48A of the upper surface Pt481A of the conductor 481a connected to the cable connection land may be raised to be substantially the same as the height of the upper surface Pt57 of the electronic component 57 as illustrated by an arrow Y11. In this case, the number of layers of the multi-layer substrate 246A need not be increased. Therefore, the manufacturing process can be simplified and the cost reduction can be achieved.

Figure 13:
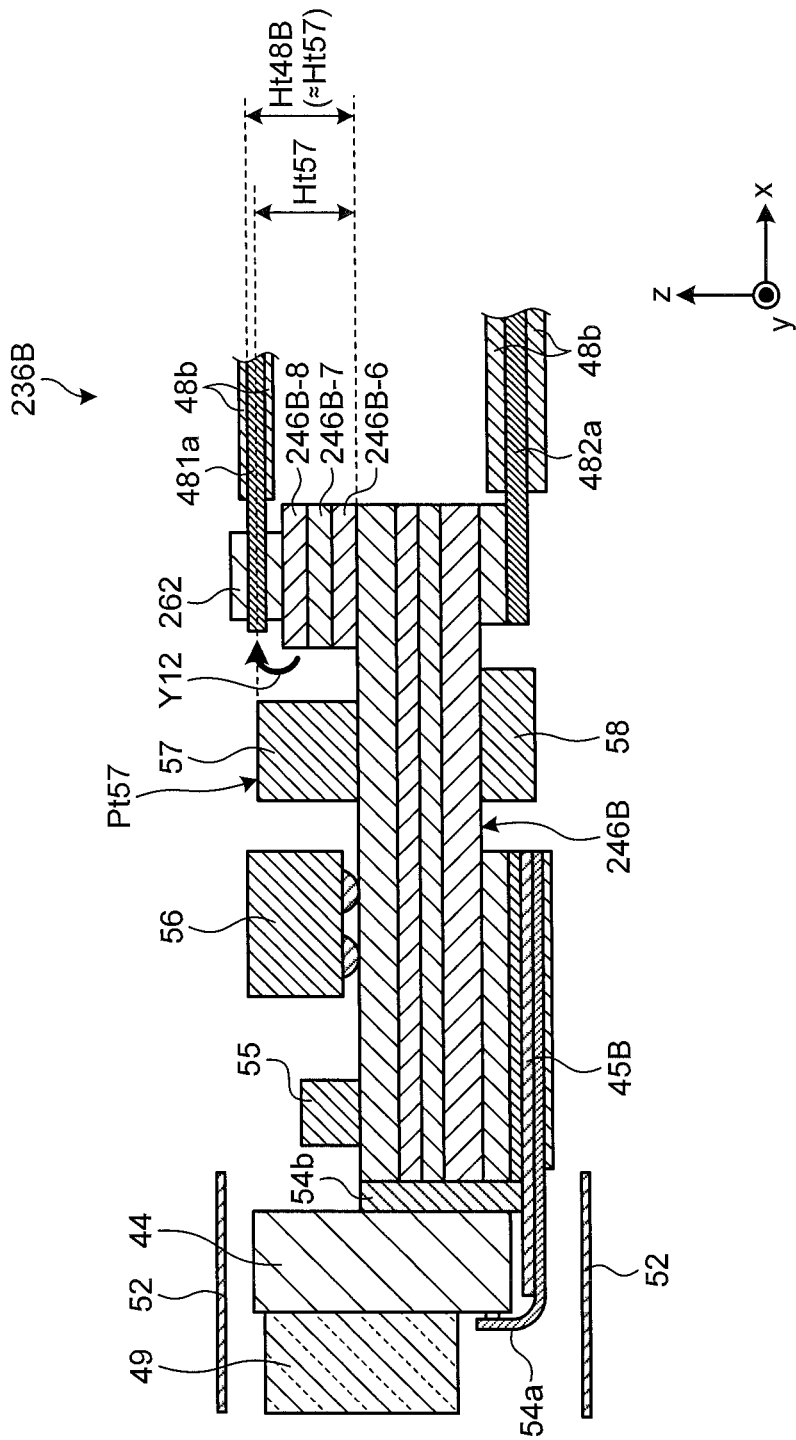
FIG. 13 is a partial cross-sectional view of another example of the imaging unit according to the second embodiment.
Figure 14:
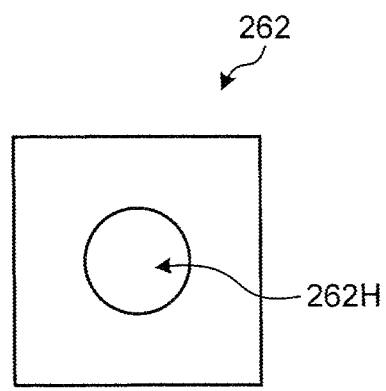
FIG. 14 is a right side view of a spacer illustrated in FIG. 13.

As in an imaging unit 236B illustrated in FIG. 13, depending on the thickness of a sixth layer 246B-6 to an eighth layer 246B-8 of a multi-layer substrate 246B, the height Ht48B of the upper surface of the conductor 481a may be adjusted to be the same as the height of the upper surface Pt57 of the electronic component 57 as illustrated by an arrow Y12 by connecting the conductor 481a to the cable connection land through a spacer 262. FIG. 14 is a right side view of the spacer 262. As illustrated in FIG. 14, the spacer 262 has a through-hole 262H, and the conductor 481a is inserted into the through-hole 262H. As illustrated in FIGS. 12 to 14, in the second embodiment, the height of the conductor 481a may be raised by mounting a metallic component on the surface of the substrate of a substrate body or a surface of any one of the layers of the multi-layer substrate and providing a cable connection land on the surface of the metallic component.

Figure 15:
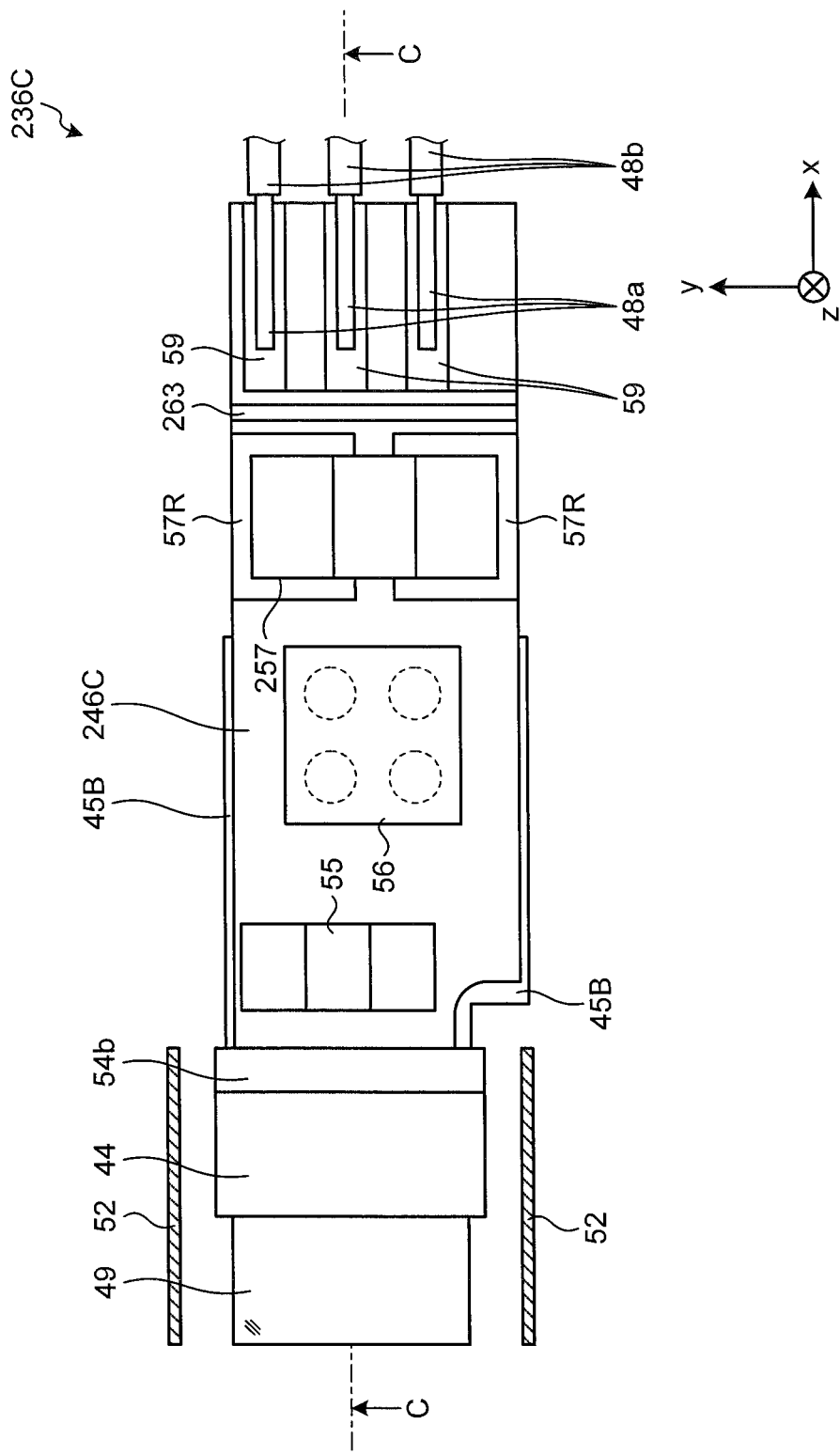
FIG. 15 is a plan view illustrating another example of the imaging unit according to the second embodiment.
Figure 16:
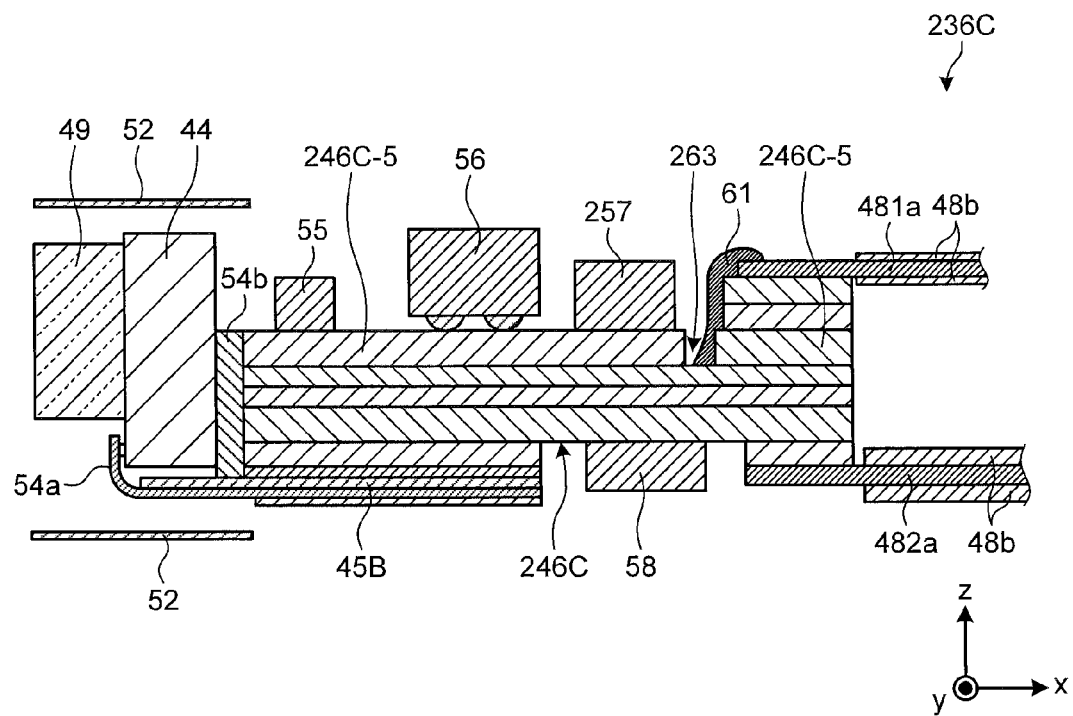
FIG. 16 is a cross-sectional view taken along line C-C in FIG. 15.

Further, as in an imaging unit 236C in FIG. 15, a groove 263 may be provided between an electronic component 257 and the cable connection land 59. FIG. 16 is a cross-sectional view taken along line C-C in FIG. 15. As illustrated in FIG. 16, the groove 263 is provided in a fifth layer 246C-5 of a multi-layer substrate 246C and the solder 61 is collected in the groove 263, so that the solder 61 does not flow to the electronic component 257. In this way, a large distance between the electronic component 257 and the cable connection land 59 may be ensured by providing the groove 263. To prevent a short-circuit between the electronic component and the cable connection land, a concave portion that can collect the solder 61 only has to be provided between the mounting surface of the electronic component 257 and the land surface of the cable connection land 59 on the upper side of the multi-layer substrate, so that it is not necessarily required to form the groove 263 over the entire length in the y axis direction of the multi-layer substrate 246C.

As in the imaging unit 236C in FIG. 15, all of the three cable connection lands may be placed within a projection area where the electronic component 257 and two component connection lands 57R of the electronic component 257 are projected in the x axis direction. Alternatively, as in an imaging unit 236D in FIG. 17, one cable connection land 259D of the three cable connection lands on a multi-layer substrate 246D may be placed outside a projection area where the electronic component 257 and the component connection lands 57R are projected in the x axis direction. In the same manner as in the first embodiment, in the second embodiment, a plurality of cable connection lands are provided on the same land surface, the plurality of cable connection lands provided on the land surface are orthogonal to the longitudinal direction of the multi-layer substrate which is the mounting substrate, and the plurality of cable connection lands are located on the same straight line in parallel with the land surface.

Figure 17:
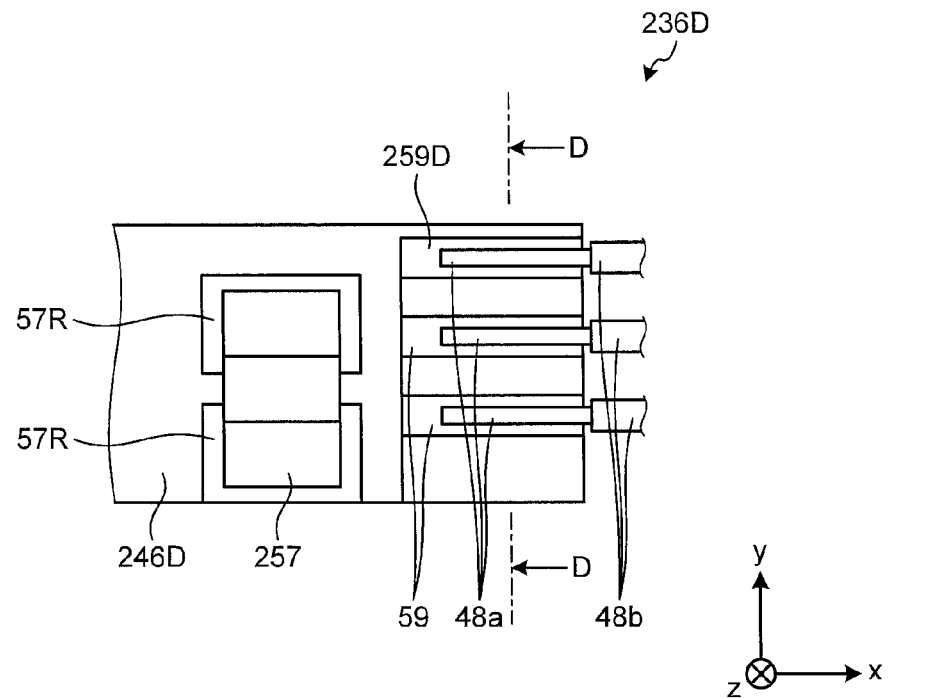
FIG. 17 is a plan view illustrating a proximal end of another example of the imaging unit according to the second embodiment.
Figure 18:
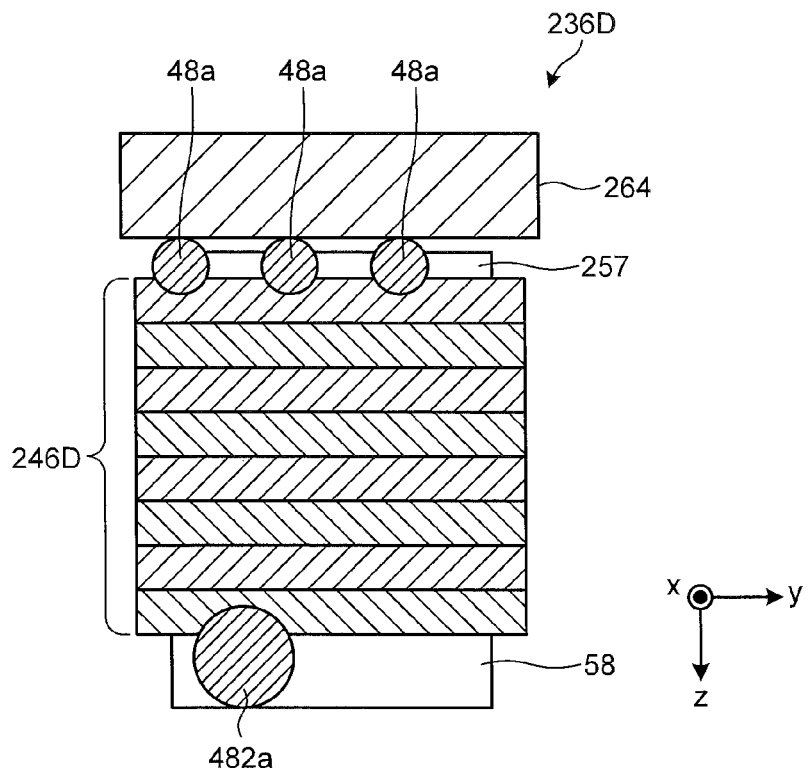
FIG. 18 is a cross-sectional view taken along line D-D in FIG. 17.

FIG. 18 is a cross-sectional view taken along line D-D in FIG. 17. As illustrated in FIG. 18, all of the upper surfaces of the three conductors 48a are arranged to be the same height as the upper surface of the electronic component 257 in both cases of the case in which all of the cable connection lands are placed within the projection area where the electronic component 257 and the component connection lands 57R are projected in the x axis direction and the case in which one cable connection land 259D is placed at a position outside the projection area where the electronic component 257 and the component connection lands 57R are projected in the x axis direction. In this case, all of the upper surfaces of the three conductors 48a are arranged to be the same height, so that it is possible to efficiently perform soldering on all of the three conductors 48a at the same time by using a pulse heat tool 264.

Figure 19:
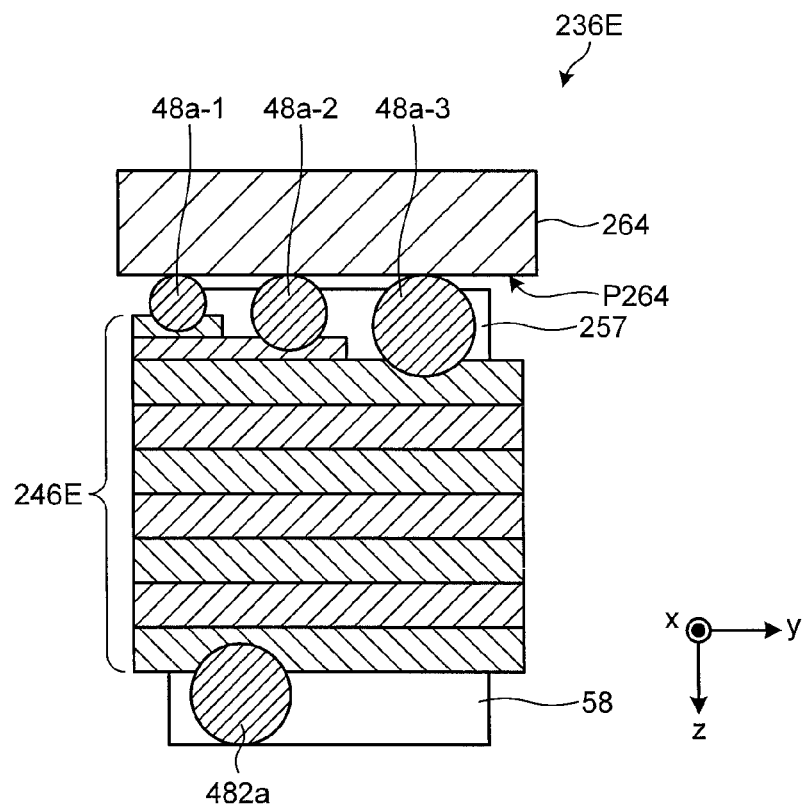
FIG. 19 is a cross-sectional view of another example of the imaging unit according to the second embodiment taken along a line located at the same position as that of D-D line in FIG. 17.

Further, as in an imaging unit 236E in FIG. 19, when connecting conductors 48a-1 to 48a-3 having a diameter different from one another, the thickness of the layer of a multi-layer substrate 246E immediately below each conductor may be adjusted so that the heights of the upper surfaces of the conductors 48a-1 to 48a-3 are arranged to be the same height. For example, for the multi-layer substrate 246E immediately below the conductor 48a-1 having the smallest outer diameter, the number of layers is set to nine. For the multi-layer substrate 246E immediately below the conductor 48a-2 having the second smallest outer diameter after the conductor 48a-1, the number of layers is set to eight. For the multi-layer substrate 246E immediately below the conductor 48a-3 having the largest outer diameter, the number of layers is set to seven. To perform soldering at the same time by using the pulse heat tool when the heights of the conductors are uneven, it is required to form unevenness corresponding to the heights of the conductors in a tool surface of the pulse heat tool. On the other hand, in the imaging unit 236E, the multi-layer substrate 246E is formed to vary the thickness of the layers according to the diameters of the signal cables so that the distance between the non-contact surface opposite to the cable connection land and the mounting surface of the electronic components in the vertical direction to the mounting surface is equal for each signal cable. As a result, the imaging unit 236E has a plurality of the land surfaces where the distance to the mounting surface in the vertical direction to the mounting surface is set such that the distance between the non-contact surface opposite to the cable connection land and the mounting surface of the electronic components in the vertical direction to the mounting surface is equal for each signal cable. Therefore, it is possible to perform soldering by using only the pulse heat tool 264 in which a tool surface P264 with which the conductor comes into contact is still flat.

In the second embodiment, a case is mainly described where when the mounting surface is an upper surface, the cable connection land is formed on a surface higher than the mounting surface of electronic components so that the cable connection land can be provided at a position away from the mounting surface of electronic components in the vertical direction to the mounting surface. However, when the cable connection land is formed on a surface different from the mounting surface of electronic components from among the surfaces of the substrate body, it is possible to prevent the solder from flowing into the electronic components, so that the surface on which the cable connection land is provided may be formed on a surface lower than the mounting surface of electronic components. In the first and the second embodiments, an imaging unit including a rigid substrate has been described. However, the substrate may be, of course, a flexible printed circuit board. In the first and the second embodiments, an example where electronic components are mounted on a multi-layer substrate has been described. However, the substrate on which the electronic components are mounted is not limited to a multi-layer substrate in which a plurality of layers are provided, but may be a rigid substrate having a single layer.

APPENDIX 1

An imaging unit including:
a solid-state imaging element including a light receiving face for receiving light;
a mounting substrate provided extending from the solid-state imaging element in an optical axis direction of the solid-state imaging element and configured to be electrically connected to the solid-state imaging element;
an electronic component mounted on an upper side of the mounting substrate and including a drive circuit for the solid-state imaging element; and a signal cable configured to be electrically connected to the electronic component, wherein on the upper side of the mounting substrate, provided are a mounting surface on which the electronic component is mounted and a land surface which is different from the mounting surface and on which a cable connection land to which the signal cable is configured to be electrically connected is provided.

APPENDIX 2

The imaging unit according to appendix 1, wherein
the land surface is provided at a position away from the mounting surface by a level difference portion in a vertical direction to the mounting surface.

APPENDIX 3

The imaging unit according to appendix 1 or 2, wherein
a distance between the mounting surface and a non-contact surface of the signal cable on an opposite side of the land surface in a vertical direction to the mounting surface is equal to a distance of the electronic component mounted closest to the signal cable from the mounting surface in the vertical direction to the mounting surface.

APPENDIX 4

The imaging unit according to any one of appendices 1 to 3, wherein
the cable connection land is provided on a proximal end side with respect to the electronic component opposite to the solid-state imaging element along the optical axis direction.

APPENDIX 5

The imaging unit according to any one of appendices 1 to 4, wherein
on the mounting surface of the mounting substrate, a metallic component is provided, and
the cable connection land is provided on a surface of the metallic component.

APPENDIX 6

The imaging unit according to any one of appendices 1 to 5, wherein
on the upper side of the mounting substrate, a concave portion is provided between the mounting surface and the land surface.

APPENDIX 7

The imaging unit according to any one of appendices 1 to 6, further including additional one or more cable connection lands, wherein
at least one of the cable connection land and the additional one or more cable connection lands is provided at a position outside a projection area where the electronic component and a component connection land on which the electronic component on the mounting surface is mounted are projected in the optical axis direction.

APPENDIX 8

The imaging unit according to any one of appendices 1 to 7, wherein
the cable connection land and additional one or more cable connection lands are provided on the same land surface, wherein
the cable connection land and the additional one or more cable connection lands on the land surface are orthogonal to a longitudinal direction of the mounting substrate and are arranged and positioned on a same straight line in parallel with the land surface.

APPENDIX 9

The imaging unit according to appendix 7 or 8, wherein
a distance between the mounting surface and a non-contact surface of the signal cable on an opposite side of the land surface in a vertical direction to the mounting surface is equal for each signal cable.

APPENDIX 10

The imaging unit according to appendix 9, wherein
the mounting substrate has the land surface and additional one or more land surfaces in which a distance to the mounting surface in the vertical direction to the mounting surface is set according to a signal cable diameter such that the distance between the mounting surface and the non-contact surface of the signal cable on the opposite side of the land surface in the vertical direction to the mounting surface is equal for each signal cable.

APPENDIX 11

An endoscope device including an insertion portion provided with the imaging unit according to any one of appendices 1 to 10 at a distal end of the insertion portion.

According to some embodiments, it is possible to provide an imaging module and an endoscope device in which a connection land and an electronic component can be arranged without extending a mounting substrate in an optical axis direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An imaging module, comprising:
a solid-state imaging element including a light receiving face for receiving light on a surface of the solid-state imaging element;
a glass lid attached to the solid-state imaging element so as to cover the light receiving face of the solid-state imaging element;
a mounting substrate including a connection portion which is located inside an imaging element projection area that is a projection area where the solid-state imaging element is projected in an optical axis direction of the solid-state imaging element and which is connected and fixed to a back surface of the solid-state imaging element on a distal end side of the mounting substrate, the mounting substrate on a rear end side being extended in the optical axis direction;

a connection substrate that is configured to electrically connect the mounting substrate to the solid-state imaging element;

a plurality of electronic components mounted on the mounting substrate;

a metallic reinforcing member that has a sleeve shape open at both ends and covers the solid-state imaging element and the connection portion of the mounting substrate along the optical axis direction in a state where an inner circumferential surface of the reinforcing member is away from the solid-state imaging element and the mounting substrate; and a solid-state imaging element holder in which an outer circumferential surface of the glass lid is fitted into an inner circumferential surface of a proximal end side of the solid-state imaging element holder to hold the solid-state imaging element, the inner circumferential surface of a distal end side of the reinforcing member being fitted into an outer circumferential surface of the proximal end side of the solid-state imaging element holder, wherein on a rear end side of the connection portion, the mounting substrate includes a protrusion portion that protrudes outside of the imaging element projection area in a state where the protrusion portion is away from a rear end of the reinforcing member by a specified distance or more, and on the rear end side of the connection portion, the plurality of electronic components are mounted on the mounting substrate such that a longitudinal direction of the plurality of electronic components is perpendicular to the optical axis direction, and the plurality of electronic components are arranged away from the rear end of the reinforcing member by the specified distance or more.

2. The imaging module according to claim 1, wherein the protrusion portion is located inside a reinforcing member projection area that is a projection area where an outer circumference of the reinforcing member is projected in the optical axis direction.

3. The imaging module according to claim 1, wherein a signal cable that is configured to be electrically connected to the solid-state imaging element is connected to the mounting substrate.

4. The imaging module according to claim 1, wherein the mounting substrate is a rigid substrate.

5. An endoscope device including an insertion portion provided with an imaging module at a distal end of the insertion portion, the imaging module comprising:

a solid-state imaging element including a light receiving face for receiving light on a surface of the solid-state imaging element;

a glass lid attached to the solid-state imaging element so as to cover the light receiving face of the solid-state imaging element;

a mounting substrate including a connection portion which is located inside an imaging element projection area that is a projection area where the solid-state imaging element is projected in an optical axis direction of the solid-state imaging element and which is connected and fixed to a back surface of the solid-state imaging element on a distal end side of the mounting substrate, the mounting substrate on a rear end side being extended in the optical axis direction;

a connection substrate that is configured to electrically connect the mounting substrate to the solid-state imaging element;

a plurality of electronic components mounted on the mounting substrate;

a metallic reinforcing member that has a sleeve shape open at both ends and covers the solid-state imaging element and the connection portion of the mounting substrate along the optical axis direction in a state where an inner circumferential surface of the reinforcing member is away from the solid-state imaging element and the mounting substrate; and a solid-state imaging element holder in which an outer circumferential surface of the glass lid is fitted into an inner circumferential surface of a proximal end side of the solid-state imaging element holder to hold the solid-state imaging element, the inner circumferential surface of a distal end side of the reinforcing member being fitted into an outer circumferential surface of the proximal end side of the solid-state imaging element holder, wherein on a rear end side of the connection portion, the mounting substrate includes a protrusion portion that protrudes outside of the imaging element projection area in a state where the protrusion portion is away from a rear end of the reinforcing member by a specified distance or more, and on the rear end side of the connection portion, the plurality of electronic components are mounted on the mounting substrate such that a longitudinal direction of the plurality of electronic components is perpendicular to the optical axis direction, and the plurality of electronic components are arranged away from the rear end of the reinforcing member by the specified distance or more.

* * * * *